US009534034B2

(12) United States Patent
Amento et al.

(10) Patent No.: US 9,534,034 B2
(45) Date of Patent: Jan. 3, 2017

(54) METHODS OF MODULATING APOPTOSIS BY ADMINISTRATION OF RELAXIN AGONISTS OR ANTAGONISTS

(75) Inventors: Edward P. Amento, Portola Valley, CA (US); Chrishan S. Samuel, Glen Waverly (AU)

(73) Assignee: Molecular Medicine Research Institute, Sunnyvale, CA (US)

( * ) Notice: Subject to any disclaimer, the term of this patent is extended or adjusted under 35 U.S.C. 154(b) by 0 days.

(21) Appl. No.: 13/399,620

(22) Filed: Feb. 17, 2012

(65) Prior Publication Data

US 2012/0238499 A1    Sep. 20, 2012

Related U.S. Application Data

(60) Continuation of application No. 12/945,685, filed on Nov. 12, 2010, now Pat. No. 8,119,136, which is a division of application No. 11/781,872, filed on Jul. 23, 2007, now Pat. No. 7,833,526, which is a division of application No. 10/398,553, filed as application No. PCT/US01/42484 on Oct. 4, 2001, now abandoned.

(60) Provisional application No. 60/242,037, filed on Oct. 20, 2000, provisional application No. 60/241,991, filed on Oct. 20, 2000, provisional application No. 60/238,232, filed on Oct. 4, 2000.

(51) Int. Cl.
| A61K 38/00 | (2006.01) |
| C07K 14/64 | (2006.01) |
| A01K 67/027 | (2006.01) |
| A61K 38/22 | (2006.01) |

(52) U.S. Cl.
CPC ........... *C07K 14/64* (2013.01); *A01K 67/0276* (2013.01); *A61K 38/2221* (2013.01); *A01K 2227/105* (2013.01); *A61K 38/22* (2013.01)

(58) Field of Classification Search
CPC ................................ A61K 38/00; A61K 38/22
USPC ........... 514/1.1, 514; 435/375; 530/300, 350
See application file for complete search history.

(56) References Cited

U.S. PATENT DOCUMENTS

| 4,758,516 A | 7/1988 | Hudson |
| 4,835,251 A * | 5/1989 | Burnier et al. ............... 530/324 |
| 4,889,818 A | 12/1989 | Gelfand |
| 5,023,321 A | 6/1991 | Hudson |
| 5,108,919 A | 4/1992 | Liu |
| 5,166,191 A | 11/1992 | Cronin |
| 5,179,195 A | 1/1993 | Hudson |
| 5,464,756 A | 11/1995 | Henner |
| 5,612,051 A | 3/1997 | Yue |
| 5,707,642 A | 1/1998 | Yue |
| 5,753,623 A | 5/1998 | Amento |
| 5,795,807 A | 8/1998 | Gardner |
| 5,811,395 A | 9/1998 | Schwabe |
| 5,863,552 A | 1/1999 | Yue |
| 5,945,402 A | 8/1999 | Cipolla |
| 5,965,405 A | 10/1999 | Winter |
| 6,048,544 A | 4/2000 | Yue |
| 6,251,863 B1 | 6/2001 | Yue |
| 6,436,448 B1 | 8/2002 | Yue |
| 2002/0022593 A1 | 2/2002 | Yue |
| 2010/0286046 A1 | 11/2010 | Medin |

FOREIGN PATENT DOCUMENTS

| CH | 661 662 A | 4/1984 |
| EP | 0 107 782 | 9/1984 |
| EP | 0 251 615 | 1/1998 |
| WO | 90/13659 | 11/1990 |
| WO | 94/29452 | 12/1994 |
| WO | 95/00645 | 1/1995 |
| WO | 95/07711 | 3/1995 |
| WO | 96/41167 A1 | 12/1996 |
| WO | 97/16549 A1 | 5/1997 |
| WO | 99/40929 | 8/1999 |

OTHER PUBLICATIONS

Sutton et al. (Ann. NY Acad. Sci. Apr. 2009; 1160: 242-9).*
Hall et al. (Biol. Reprod. May-Jun. 1990; 42 (5-6): 769-74).*
Nistri et al. (Pharmacol Res. Jan. 2008; 57 (1): 43-8).*
Skolnick et al. (Trends in Biotechnology 2000; 18: 34-39).*
Bowie et al. (Science 1990; 257: 1306-1310).*
Burgess et al. (Journal of Cell Biology 1990; 111: 2129-2138).*
Lazar et al. (Molecular and Cellular Biology, 1988, 8: 1247-1252).*
Luque et al. (Biochemistry. Nov. 19, 2002; 41 (46): 13663-13671).*
Vucic et al. (J. Biol. Chem. Dec. 18, 1998; 273 (51): 33915-33921).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Winn, R.J., et al., "Individual and Combined Effects of Relaxin, Estrogen, and Progesterone in Ovariectomized Gilts. I. Effects on the Growth, Softening, and Histological Properties of the Cervix," Endocrinology 135(3):1241-1249, Sep. 1994.
Winn, R.J., et al., "Individual and Combined Effects of Relaxin, Estrogen, and Progesterone in Ovariectomized Gilts. II. Effects on Mammary Development," Endocrinology 135(3):1250-1255, Sep. 1994.
Zhao, L., et al., "Mice Without a Functional Relaxin Gene Are Unable to Deliver Milk to Their Pups," Endocrinology 140(1):445-453, Jan. 1999.
Bell, R.J., et al., "A Randomized, Double-Blind Placebo-Controlled Trial of the Safety of Vaginal Recombinant Human Relaxin for Cervical Ripening," Obstetrics and Gynecology 82(3):328-333, Sep. 1993.

(Continued)

*Primary Examiner* — Stephen Rawlings
(74) *Attorney, Agent, or Firm* — Christensen O'Connor Johnson Kindness PLLC

(57) ABSTRACT

The present invention relates to the discovery that relaxin is associated with the development or maturation of body tissues. Knockouts of the gene encoding relaxin result in various abnormalities in the development of various tissues. The present invention provides methods of modulating apoptosis by administering a relaxin agonist or antagonist to a subject.

7 Claims, 2 Drawing Sheets

(56) References Cited

OTHER PUBLICATIONS

Ben-Hur, H., et al., "Localization of Estrogen Receptors in Long Bones and Vertebrae of Human Fetuses," Calcified Tissue International 53(2):91-96, Aug. 1993.
Bibby, M.C., "Orthotopic Models of Cancer for Preclinical Drug Evaluation: Advantages and Disadvantages," European Journal of Cancer 40(6):852-857, Apr. 2004.
Bryant-Greenwood, G.D., and C. Schwabe, "Human Relaxins: Chemistry and Biology," Endocrine Reviews 15(1):5-26, Feb. 1994.
Bryant-Greenwood, G.D., et al., "Sequential Appearance of Relaxin, Prolactin and IGFBP-1 During Growth and Differentiation of the Human Endometrium," Molecular and Cellular Endocrinology 95(1-2):23-29, Sep. 1993.
Büllesbach, E.E., et al., "The Receptor-Binding Site of Human Relaxin II. A Dual Prong-Binding Mechanism," Journal of Biological Chemistry 267(32):22957-22960, Nov. 1992.
Burgess, W.H., et al., "Possible Dissociation of the Heparin-Binding and Mitogenic Activities of Heparin-Binding (Acidic Fibroblast) Growth Factor 1 From Its Receptor-Binding Activities by Site-Directed Mutagenesis of a Single Lysine Residue," Journal of Cell Biology 111(5 Pt. 1):2129-2138, Nov. 1990.
Chen, S.A., et al., "The Pharmacokinetics of Recombinant Human Relaxin in Nonpregnant Women After Intravenous, Intravaginal, and Intracervical Administration," Pharmaceutical Research 10(6):834-838, Jun. 1993.
Colon, J.M., et al., "Relaxin Secretion Into Human Semen Is Independent of Gonadotropin Stimulation," Biology of Reproduction 50(1):187-192, Jan. 1994.
Dennis, C., "Off by a Whisker," Nature 442:739-741, Aug. 2006.
Golub, M.S., et al., "Effect of Short-Term Infusion of Recombinant Human Relaxin on Blood Pressure in the Late-Pregnant Rhesus Macaque (Macaca mulatta)," Obstetrics and Gynecology 83(1):85-88, Jan. 1994.
Guo, H.H., "Protein Tolerance to Random Amino Acid Change," Proceedings of the National Academy of Sciences of the United States of America (PNAS) 101(25):9205-9210, Jun. 2004.
Gura, T., "Systems for Identifying New Drugs Are Often Faulty," Science 278(5340):1041-1042, Nov. 1997.
Hagemann, T., et al., "Relaxin Enhances In Vitro Invasiveness of Breast Cancer Cell Lines and Expression of Matrix Metalloproteases," Onkologie: Int'l Journal for Cancer Research and Treatment, Sonderheft 7 (Deutsche und Österreichische Gesellschaften für Hämatologie und Onkologie Gemeinsame Jahrestagung, Graz, Austria, Oct. 21-25, 2000), vol. 23, Oct. 2000, Abstract 0594, p. 156.
Hall, J.A., et al., "Influence of Ovarian Steroids on Relaxin-Induced Uterine Growth in Ovariectomized Gilts," Endocrinology 130(6):3159-3166, Jun. 1992.
Hansell, D.J., and E.P. Gelmann, "The Role of Relaxin in Promoting Prostate Cancer Cellular Motility and Wound Healing," Poster Session Y 110, in "Breast and Prostate Cancer II," Journal of Cellular Biochemistry (Supplement: Keystone Symposia on Molecular & Cellular Biology) 56(Suppl. 18D):230, Feb. 1994.
Huang, C., et al., "Stimulation of Collagen Secretion by Relaxin and Effect of Oestrogen on Relaxin Binding in Uterine Cervical Cells of Pigs," Journal of Reproduction and Fertility 98(1):153-158, May 1993.
Jauniaux, E., et al., "The Role of Relaxin in the Development of the Uteroplacental Circulation in Early Pregnancy," Obstetrics and Gynecology 84(3):338-342, Sep. 1994.
Johnson, M.R., et al., "Relationship Between Ovarian Steroids, Gonadotrophins and Relaxin During the Menstrual Cycle," Acta Endocrinologica 129(2):121-125, Aug. 1993.
Johnson, M.R., et al., "The Regulation of Plasma Relaxin Levels During Human Pregnancy," Journal of Endocrinology 142(2):261-265, Aug. 1994.
Kelland, L.R., "Of Mice and Men: Values and Liabilities of the Athymic Nude Mouse Model in Anticancer Drug Development," European Journal of Cancer 40(6):827-836, Apr. 2004.

Kibblewhite, D., et al, "The Effect of Relaxin on Tissue Expansion," Archives of Otolaryngology—Head and Neck Surgery 118(2):153-156, Feb. 1992.
Krajewski, S., et al., "Immunohistochemical Determination of in Vivo Distribution of Bax, a Dominant Inhibitor of Bcl-2," American Journal of Pathology 145(6):1323-1336, Dec. 1994.
Lane, B., et al., "Decidualization of Human Endometrial Stromal Cells in Vitro: Effects of Progestin and Relaxin on the Ultrastructure and Production of Decidual Secretory Proteins," Human Reproduction 9(2):259-266, Feb. 1994.
Lanzafame, F., et al., "Pharmacological Stimulation of Sperm Motility," Human Reproduction 9(2):192-199, Feb. 1994.
Lazar, E. et al. "Transforming Growth Factor α: Mutation of Aspartic Acid 47 and Leucine 48 Results in Different Biological Activities," Molecular and Cellular Biology 8(3):1247-1252, Mar. 1988.
Lee, A.B., et al., "Monoclonal Antibodies Specific for Rat Relaxin. VI. Passive Immunization With Monoclonal Antibodies Throughout the Second Half of Pregnancy Disrupts Histological Changes Associated With Cervical Softening at Parturition in Rats," Endocrinology 130(4):2386-2391, Apr. 1992.
Luque, L.E., et al., "A Highly Conserved Arginine Is Critical for the Functional Folding of Inhibitor of Apoptosis (IAP) BIR Domains," Biochemistry 41(46):13663-13671, Nov. 2002.
MacLennan, A.H., et al., "Ripening of the Human Cervix and Induction of Labor with Intracervical Purified Porcine Relaxin," Obstetrics and Gynecology 68(5):598-601, Nov. 1986.
Neuberger, M.S., et al, "Recombinant Antibodies Possessing Novel Effector Functions," Nature 312(5995):604-608, Dec. 1984.
O'Day-Bowman, M.B., et al., "Hormonal Control of the Cervix in Pregnant Gilts. III. Relaxin's Influence on Cervical Biochemical Properties in Ovariectomized Hormone-Treated Pregnant Gilts," Endocrinology 129(4):1967-1976, Oct. 1991.
Palejwala, S., et al., "Demonstration of a Relaxin Receptor and Relaxin-Stimulated Tyrosine Phosphorylation in Human Lower Uterine Segment Fibroblasts," Endocrinology 139(3):1208-1212, Mar. 1998.
Park, J.M., et al., "Effects of Relaxin on the Fertilization Capacity of Human Spermatozoa," American Journal of Obstetrics and Gynecology 158(4):974-979, Apr. 1988.
Petersen, L.K., et al., "Normal Serum Relaxin in Women With Disabling Pelvic Pain During Pregnancy," Gynecologic and Obstetric Investigation 38(1):21-23, 1994.
Peterson, J.K., and P.J. Houghton, "Integrating Pharmacology and in Vivo Cancer Models in Preclinical and Clinical Drug Development," European Journal of Cancer 40(6):837-844, Apr. 2004.
Poisner, A.M., et al., "Relaxin Stimulates the Synthesis and Release of Prorenin From Human Decidual Cells: Evidence for Autocrine/Paracrine Regulation," Journal of Clinical Endocrinologic Metabolism 70(6):1765-1767, Jun. 1990.
Saijo, N., "What are the Reasons for Negative Phase III Trials of Molecular-Target-Based Drugs?" Cancer Science 95(10):772-776, Oct. 2004.
Saiki, R.K., et al., "Primer-Directed Enzymatic Amplification of DNA With a Thermostable DNA Polymerase," Science 239(4839):487-491, Jan. 1988.
Saugstad, L.F., "Is Persistent Pelvic Pain and Pelvic Joint Instability Associated With Early Menarche and With Oral Contraceptives?" European Journal of Obstetrics, Gynecology, and Reproductive Biology 41(3):203-206, Oct. 1991.
Saxena, P.R., et al., "Is the Relaxin System a Target for Drug Development? Cardiac Effects of Relaxin," Trends in Pharmacological Science 14(6):231-232, Jun. 1993.
Schuh, J.C., "Trials, Tribulations, and Trends in Tumor Modeling in Mice," Toxicologic Pathology 32(Suppl. 1):53-66, Mar.-Apr. 2004.
Skolnick, J., and J.S. Fetrow, "From Genes to Protein Structure and Function: Novel Applications of Computational Approaches in the Genomic Era," Trends in Biotechnology 18(1):34-39, Jan. 2000.
Sokol, R.Z., et al., "Immunohistochemical Localization of Relaxin in Human Prostate," Journal of Histochemistry and Cytochemistry 37(8):1253-1255, Aug. 1989.

(56) References Cited

OTHER PUBLICATIONS

Takada, I., et al., "Alteration of a Single Amino Acid in Peroxisome Proliferator-Activated Receptor-α (PPARα) Generates a PPARδ Phenotype," Molecular Endocrinology 14(5):733-740, May 2000.

Tashima, L.S., et al., "Human Relaxins in Normal, Benign and Neoplastic Breast Tissue," Journal of Molecular Endocrinology 12(3):351-364, Jun. 1994.

Traeger, G.W., et al., "Biology of Relaxin and Its Role in the Human," in Bigazzi et al. (eds.), Proceedings of the 1st International Conference on Human Relaxin, Florence, Italy, Sep. 30-Oct. 2, 1982, pp. 42-55.

Unemori, E.N., et al., "Human Relaxin Decreases Collagen Accumulation In Vivo in Two Rodent Models of Fibrosis," Journal of Investigative Dermatology 101(3):280-285, Sep. 1993.

Vucic, D., et al., "A Mutational Analysis of the Baculovirus Inhibitor of Apoptosis Op-IAP," Journal of Biological Chemistry 273(18):33915-33921, Dec. 1998.

Wang-Lee, J.L., et al., "Regulation of Urokinase- and Tissue-Type Plasminogen Activator by Relaxin in the Uterus and Cervix of the Prepubertal Gilt," Journal of Reproduction and Fertility 114(1):119-125, Sep. 1998.

Winn, R.J., et al., "Hormonal Control of the Cervix in Pregnant Gilts. IV. Relaxin Promotes Changes in the Histological Characteristics of the Cervix That Are Associated With Cervical Softening During Late Pregnancy in Gifts," Endocrinology 133(1):121-128, Jul. 1993.

\* cited by examiner

| | | | | | | | | | | | | | | | | | | |
|---|---|---|---|---|---|---|---|---|---|---|---|---|---|---|---|---|---|---|
| Leu | Val | Glu | Ala | Leu | Tyr | Leu | Val | Cys | Gly | Glu | Arg | Gly | Phe | Phe | Tyr | Thr | Pro | Lys |
| Leu | Val | Arg | Ala | Gln | Ile | Ala | Ile | Cys | Gly | Met | Ser | Thr | Trp | Ser | Lys | Arg | 30 Arg | Ser |
| Leu | Val | Arg | Ala | Gln | Ile | Ala | Ile | Cys | Gly | Met | Ser | Thr | Trp | Ser | Lys | Arg | Arg | Ser |
| Leu | Val | Arg | Leu | Trp | Val | Glu | Ile | Cys | Gly | Ser | Val | Ser | Trp | Gly | Arg | Thr | Arg | Leu |
| Tyr | Ala | Arg | Ala | Trp | Ile | Glu | Val | Cys | Gly | Ser | Ala | | | | | | | |
| Phe | Ile | Arg | Ala | Ile | Phe | Ala | Cys | Gly | Ser | | | | | | | | | |
| Phe | Ile | Arg | Ala | Ile | Tyr | Ser | Ala | Cys | Cys | Gly | Arg | | | | | | | |
| Cys | Ser | Leu | Tyr | Gln | Leu | Glu | Asn | Tyr | Cys 100 | Asn | | | | | | | | |
| Cys | Thr | Lys | Arg | Ser | Leu | Ala | Lys | Tyr | Cys | | | | | | | | | |
| Cys | Thr | Lys | Arg | Ser | Leu | Ala | Arg | Phe | Cys | | | | | | | | | |
| Cys | Ile | Arg | Lys | Asp | Ile | Arg | Arg | Leu | Cys | | | | | | | | | |
| Cys | Thr | Arg | Ser | Ile | Asp | Ile | Arg | Thr | Leu | Cys | | | | | | | | |
| Cys | Thr | Lys | Lys | Asp | Ile | Arg | Lys | Ala | Leu | Cys | | | | | | | | |
| Cys | Thr | Lys | Lys | Asp | Ile | Ser | Val | Leu | Cys | | | | | | | | | |
| Cys | Thr | Arg | Lys | Ser | Ile | Ser | Ile | Leu | Cys | | | | | | | | | |

SEQUENCE LISTING

```
<160> NUMBER OF SEQ ID NOS: 14

<210> SEQ ID NO 1
<211> LENGTH: 38
<212> TYPE: PRT
<213> ORGANISM: Homo sapiens

<400> SEQUENCE: 1

Ala Val Ala Ala Lys Trp Lys Asp Asp Val Ile Lys Leu Cys Gly Arg
1               5                   10                  15

Glu Leu Val Arg Ala Gln Ile Ala Ile Cys Gly Met Ser Thr Trp Ser
            20                  25                  30

Lys Arg Ser Leu Ser Gln
        35

<210> SEQ ID NO 2
<211> LENGTH: 27
<212> TYPE: PRT
<213> ORGANISM: Homo sapiens

<400> SEQUENCE: 2

Lys Lys Arg Arg Pro Tyr Val Ala Leu Phe Glu Lys Cys Cys Leu Ile
1               5                   10                  15

Gly Cys Thr Lys Arg Ser Leu Ala Lys Tyr Cys
            20                  25

<210> SEQ ID NO 3
<211> LENGTH: 38
<212> TYPE: PRT
<213> ORGANISM: Homo sapiens

<400> SEQUENCE: 3

Ala Val Ala Asp Ser Trp Met Glu Glu Val Ile Lys Leu Cys Gly Arg
1               5                   10                  15

Glu Leu Val Arg Ala Gln Ile Ala Ile Cys Gly Met Ser Thr Trp Ser
            20                  25                  30

Lys Arg Ser Leu Ser Gln
        35

<210> SEQ ID NO 4
<211> LENGTH: 27
<212> TYPE: PRT
<213> ORGANISM: Homo sapiens

<400> SEQUENCE: 4

Lys Lys Arg Gln Leu Tyr Ser Ala Leu Ala Asn Lys Cys Cys His Val
1               5                   10                  15

Gly Cys Thr Lys Arg Ser Leu Ala Arg Phe Cys
            20                  25

<210> SEQ ID NO 5
<211> LENGTH: 35
<212> TYPE: PRT
<213> ORGANISM: Homo sapiens
```

-continued

<400> SEQUENCE: 5

Ala Ala Ala Phe Val Asn Gln His Leu Cys Gly Ser His Leu Val Glu
1               5                   10                  15

Ala Leu Tyr Leu Val Cys Gly Glu Arg Gly Phe Phe Tyr Thr Pro Lys
            20                  25                  30

Thr Arg Arg
        35

<210> SEQ ID NO 6
<211> LENGTH: 23
<212> TYPE: PRT
<213> ORGANISM: Homo sapiens

<400> SEQUENCE: 6

Lys Arg Gly Ile Val Glu Gln Cys Cys Thr Ser Ile Cys Ser Leu Tyr
1               5                   10                  15

Gln Leu Glu Asn Tyr Cys Asn
            20

<210> SEQ ID NO 7
<211> LENGTH: 34
<212> TYPE: PRT
<213> ORGANISM: Porcine

<400> SEQUENCE: 7

Gln Ser Thr Asn Asp Phe Ile Lys Ala Cys Gly Arg Glu Leu Val Arg
1               5                   10                  15

Leu Trp Val Glu Ile Cys Gly Ser Val Ser Trp Gly Arg Thr Ala Leu
            20                  25                  30

Ser Leu

<210> SEQ ID NO 8
<211> LENGTH: 27
<212> TYPE: PRT
<213> ORGANISM: Porcine

<400> SEQUENCE: 8

Lys Lys Arg Leu Phe Arg Met Thr Leu Ser Glu Lys Cys Cys Gln Val
1               5                   10                  15

Gly Cys Ile Arg Lys Asp Ile Ala Arg Leu Cys
            20                  25

<210> SEQ ID NO 9
<211> LENGTH: 37
<212> TYPE: PRT
<213> ORGANISM: Rattus

<400> SEQUENCE: 9

Arg Val Ser Glu Glu Trp Met Asp Gln Val Ile Gln Val Cys Gly Arg
1               5                   10                  15

Gly Tyr Ala Arg Ala Trp Ile Glu Val Cys Gly Ala Ser Val Gly Arg
            20                  25                  30

Leu Ala Leu Ser Gln
        35

<210> SEQ ID NO 10
<211> LENGTH: 27
<212> TYPE: PRT
<213> ORGANISM: Rattus

```
<400> SEQUENCE: 10

Lys Lys Arg Gln Ser Gly Ala Leu Leu Ser Glu Gln Cys Cys His Ile
1               5                   10                  15

Gly Cys Thr Arg Arg Ser Ile Ala Lys Leu Cys
            20                  25

<210> SEQ ID NO 11
<211> LENGTH: 27
<212> TYPE: PRT
<213> ORGANISM: Odontaspis taurus

<400> SEQUENCE: 11

Gln Ser Leu Ser Asn Ala Gly Ser Gly Ile Lys Leu Cys Gly Arg Gly
1               5                   10                  15

Phe Ile Arg Ala Ile Phe Ala Cys Gly Ser Arg
            20                  25

<210> SEQ ID NO 12
<211> LENGTH: 24
<212> TYPE: PRT
<213> ORGANISM: Odontaspis taurus

<400> SEQUENCE: 12

Ala Thr Ser Pro Ala Met Ser Ile Lys Cys Cys Ile Tyr Gly Cys Thr
1               5                   10                  15

Lys Lys Asp Ile Ser Val Leu Cys
            20

<210> SEQ ID NO 13
<211> LENGTH: 23
<212> TYPE: PRT
<213> ORGANISM: Squalus acanthias

<400> SEQUENCE: 13

Gln Asn Ala Glu Pro Gly Ile Lys Leu Cys Gly Arg Glu Phe Ile Arg
1               5                   10                  15

Ala Val Ile Tyr Ser Cys Gly
            20

<210> SEQ ID NO 14
<211> LENGTH: 24
<212> TYPE: PRT
<213> ORGANISM: Squalus acanthias

<400> SEQUENCE: 14

Glu Gly Ser Pro Gly Met Ser Ser Lys Cys Cys Thr Tyr Gly Cys Thr
1               5                   10                  15

Arg Lys Asp Ile Ser Ile Leu Cys
            20
```

METHODS OF MODULATING APOPTOSIS BY ADMINISTRATION OF RELAXIN AGONISTS OR ANTAGONISTS

CROSS-REFERENCES TO RELATED APPLICATIONS

This application is a continuation of U.S. application Ser. No. 12/945,685, filed Nov. 12, 2010, now U.S. Pat. No. 8,119,136, which is a divisional of U.S. application Ser. No. 11/781,872, filed Jul. 23, 2007, now U.S. Pat. No. 7,833,526, which is a divisional of U.S. application Ser. No. 10/398,553, filed Sep. 22, 2003, now abandoned, which is a U.S. national stage application under 35 U.S.C. §371 of International Application No. PCT/US01/42484, filed Oct. 4, 2001, which claims priority from Provisional Application No. 60/238,232 filed Oct. 4, 2000, Provisional Application No. 60/241,991 filed Oct. 20, 2000, and Provisional Application No. 60/242,037, filed Oct. 20, 2000, the disclosures of which are incorporated herein by reference.

BACKGROUND

The growth and development of normal tissues is achieved by programmed cell proliferation, differentiation and cell death. Cell proliferation and differentiation are required for the formation of new cells and tissues. Conversely, programmed cell death, also referred to as apoptosis, is required to remove existing cells, including immature or damaged cells. Apoptosis naturally occurs in virtually all tissues of the body. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

The disruption of the genetic program, by either abnormally increasing or decreasing rate of cell proliferation and/or apoptosis can result in abnormal tissue development. For example, decreases in cell proliferation below normal levels can lead to immature tissues and other tissue abnormalities. Increases in cell proliferation above normal levels are thought to be major events in the development of neoplasia and cancer, as well as other cell proliferative disorders. Abnormal increases in apoptosis can also lead to precancerous lesions. Precancerous lesions include lesions of the breast (that can develop into breast cancer), lesions of the prostate (that can develop into prostate cancer) or skin (that can develop into malignant melanoma or basal cell carcinoma), colonic adenomatous polyps (that can develop into colon cancer), and other such neoplasia. Such lesions exhibit a strong tendency to develop into malignant tumors or cancer.

Precancerous lesions can result from an accumulation of insults to existing cells in various tissues of the body. Such insults can include exposure to sunlight, radiation, mutagens and carcinogens normally found in the diet, chemicals such as pesticides, herbicides, preservatives, and the like. These insults can result in the accumulation of mutations in the cells, which can lead to hyperplastic conditions (i.e., abnormal increases in cell number), such as, for example, hyperplasia of liver, kidney, spleen, thymus, intestine, lung or prostate tissues. The down-regulation of apoptosis can also lead to the accumulation of cells in these hyperplastic conditions.

An abnormal increase in apoptosis can interfere with normal development and/or differentiation of tissues. For example, apoptosis is required during pregnancy and for maturation of the male reproductive tract tissues. An abnormal increase in apoptosis can also interfere with the formation of new cells and tissues, thereby preventing normal tissue maturation or development.

Thus, there is a need for methods of modulating apoptosis by administering agonists or antagonists of apoptosis. In particular, there is a need for methods of treating conditions associated, directly or indirectly, with abnormally high or low rates of apoptosis. The present invention satisfies this need by providing methods for the administration of relaxin agonists or antagonists to treat relaxin-associated tissue abnormalities by modulating apoptosis in such tissues.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention relates to the discovery that relaxin is associated with the development of body tissues. Knockouts of the gene encoding relaxin result in various abnormalities in the development of various body tissues, including smaller size of, increased collagen deposition in, and immaturity of such tissues. Conversely, relaxin-responsive cell accumulation leads to abnormalities in body tissues. The present invention provides methods of modulating apoptosis in tissues by administering a relaxin agonist or a relaxin antagonist.

In one aspect, the present invention provides methods for modulating apoptosis in a subject by administering to a subject in need thereof an effective amount of a relaxin agonist for a period of time sufficient to decrease apoptosis in cells expressing a relaxin receptor. Tissues which are typically affected by the administration of the relaxin agonist useful in methods according to the present invention include, for example, liver, kidney, spleen, thymus, brain, heart, intestine, skin, lung, the male reproductive tract, and the female reproductive tract. Male reproductive tract tissues include, for example, prostatic, epididymal, seminiferous tissues, tissues of the testes, and the like. Female productive tract tissues include, for example, uterus, cervix, the interpubic ligament, connective tissues within the pelvic girdle, and the like.

In certain embodiments, the administration of the relaxin agonist typically reduces the number of apoptotic cells. In other embodiments, the relaxin agonist stimulates maturation of the tissue. For example, a relaxin agonist can stimulate maturation of male reproductive tract tissue, such as prostatic tissue, epididymal tissue, seminiferous tissue, testicular tissue or sperm. In an embodiment, the maturation results in an increase in cell number in an under-developed testes, such as, for example, an increase in the number of mature testicular cells. In another embodiment, maturation of male reproductive tract tissue results in an increase in the number of viable sperm cells, as compared with tissue not contacted with the relaxin agonist. In yet another embodiment, fibrosis can be reduced by the relaxin agonist, and/or excessive collagen deposition can be reduced.

The subject in need of administration of the relaxin agonist can have a relaxin-deficient condition, such as, for example, immature tissue, excessive collagen deposition and/or a low sperm count. For example, the immature tissue can be immature male productive tissue (e.g., underdeveloped testes). Such immature tissue can be present in an otherwise mature or immature animal.

The relaxin agonist can be relaxin, a relaxin analog, a small molecule relaxin effector or a relaxin nucleic acid. The relaxin is typically vertebrate relaxin and more typically is human relaxin.

Compositions comprising a relaxin agonist useful in the methods according to the present invention can be formulated for administration, for example, by infusion, injection, oral delivery, nasal delivery as well as intrapulmonary, rectal, transdermal, interstitial or subcutaneous delivery. Such compositions also can be formulated for delayed release of the relaxin agonists into the tissues and circulation of the subject. Particular embodiments comprise compositions formulated for infusion or injection, or by intrapulmonary, subcutaneous or transdermal delivery. In certain embodiments, nucleic acids encoding relaxin agonists can formulated for administration to the subject in a vector encoding the relaxin agonist. For example, the vector can be an expression vector which expresses the relaxin agonist in the cells. Alternatively, relaxin or relaxin analog nucleic acids can be formulated for delivery to the subject. The subjects can be pre-pubescent or post-pubescent.

In another aspect, the present invention provides methods for modulating apoptosis in a subject in need thereof by administering an effective amount of a relaxin antagonist for a period of time sufficient to increase apoptosis in a cell population expressing a relaxin receptor. In an embodiment, the relaxin antagonist inhibits binding of relaxin to relaxin receptor. In another embodiment, the relaxin antagonist reduces relaxin-associated tissue remodeling.

Tissues which are typically affected by the administration of the relaxin antagonist useful in methods according to the present invention include, for example, liver, kidney, spleen, thymus, brain, heart, intestine, skin, lung, the male reproductive tract, the female reproductive tract, and the like. Male reproductive tract tissues include, for example, prostatic, epididymal, seminiferous tissues, tissues of the testes, and the like. In certain embodiments, the male reproductive tract tissue can be prostatic tissue, and can be mature or immature. Suitable target female productive tract tissues include, for example, uterus, cervix, the interpubic ligament, connective tissues within the pelvic girdle, and the like. Alternatively, the cell population can comprise cells expressing a relaxin receptor such as, for example, fibroblasts, osteoblasts, monocytes epithelial cells, endothelial cells, and the like.

The relaxin antagonist can be, for example, a relaxin binding agent, a relaxin receptor binding agent, a relaxin antisense nucleic acid, and the like. The relaxin binding agent can be, for example, an anti-relaxin antibody, a soluble relaxin receptor, a small molecule relaxin antagonist, and the like. The relaxin receptor binding agent can be, for example, an anti-relaxin receptor antibody, a relaxin analog, a small molecule relaxin receptor antagonist, and the like. Antibodies that bind relaxin or relaxin receptor can include, for example, polyclonal antibodies, monoclonal antibodies, an Fab, Fab', an F(ab')2, an Fv, a single heavy chain, a chimeric antibody, and the like.

Another aspect provides a human relaxin analog consisting essentially of shortened and/or modified forms of the natural B and/or A peptide chains.

Investigations with both pig and human relaxin (H1) show that relaxin activity may be present with human A chains as short as A(10-24) (Amino acids 14 to 28 of SEQ ID NO:2) and B chains as short as B(10-22)(Amino acids 14 to 26 of SEQ ID NO:1) although the expected practical minima are respectively A(4-24)(Amino acids 8 to 28 of SEQ ID NO:2) and B(4-23)(Amino acids 8 to 27 of SEQ ID NO:1). The peptide A(4-24)-B(1-25)(chain A=amino acids 8 to 28 of SEQ ID NO:2 and chain B=amino acids 5 to 29 of SEQ ID NO:1) is already known to have relaxin activity.

In general, for the present relaxin structure (H2) the A chain can be varied from A(1-24)(Amino acids 4 to 27 of SEQ ID NO:4) to A(10-24)(Amino acids 13 to 27 of SEQ ID NO:4) and B chain from B(-1-32)(Amino acids 4 to 36 of SEQ ID NO:3) to B(10-22)(Amino acids 14 to 26 of SEQ ID NO:3).

The preferred combinations are derived from:

| A | B |
|---|---|
| any of (1-24)(aa 4 to 27 of SEQ ID NO:4) (2-24)(aa 5 to 27 of SEQ ID NO:4) (3-24)(aa 6 to 27 of SEQ ID NO:4) | with any of (-1-23)(aa 4 to 27 of SEQ ID NO:3) up to (-1-32)(aa 4 to 36 of SEQ ID NO:3) |

Compositions comprising a relaxin antagonist useful in the methods of the present invention can be formulated for administration, for example, by infusion, injection, oral delivery, nasal delivery as well as intrapulmonary, rectal, transdermal, interstitial or subcutaneous delivery. Compositions can also be formulated for delayed release of the relaxin antagonist into the tissues and circulation of the subject. Particular embodiments comprise compositions formulated for infusion or injection or by intrapulmonary, subcutaneous or transdermal delivery.

In certain embodiments, nucleic acids encoding relaxin antagonists can also be administered to the subject in a vector encoding the relaxin antagonist. In one embodiment, the vector is an expression vector which expresses the relaxin antagonist in the cell population. Alternatively, relaxin or relaxin receptor antisense nucleic acids can be delivered directly to the subject, according to any of the methods described above. In a typical embodiment, administration of the relaxin antagonist increases apoptosis to reduce unwanted cell accumulation. For example, the unwanted cells can be hyperplasia, hypertrophy, cancer or neoplasia.

DESCRIPTION OF THE FIGURE

FIG. 1 shows a comparison of the amino acid sequences of the B and A chains between the two human relaxin genes (SEQ ID NOs: 1 and 3, and 2 and 4, respectively), human insulin (SEQ ID NOs: 5 and 6), and other members of the relaxin family. Boxed areas highlight residue which are conserved between the two human relaxin genes and the' relaxin family. Arrows indicate probable sites of proteolytic cleavage with confirmation by protein sequencing data of the amino terminal residue of the B and A chains of porcine (SEQ ID NOs: 7 and 8; Schwabe et al., *Biochem. Biophys. Res. Commun.* 7-5: 503-510, 1977; James et al., 1977), rat (SEQ ID NOs: 9 and 10; John et al., *Endocrinology* 108: 726-729, 1981), shark (SEQ ID NOs: 11 and 12; Schwabe et al., 1982) and dogfish relaxins (SEQ ID NOs: 13 and 14; Schwabe et al., *Amer. N.Y. Acad. Sci.* 380: 6-12, 1982).

DEFINITIONS

Prior to setting forth the invention in more detail, it may be helpful to a further understanding of the invention to set forth definitions of certain terms as used hereinafter.

The term "nucleic acid" refers to a polymer composed of a multiplicity of nucleotide units (ribonucleotide or deoxyribonucleotide or related structural variants) linked via phosphodiester bonds. A nucleic acid can be of substantially any length, typically from about six (6) nucleotides to about 10$^9$ nucleotides, or larger. Unless otherwise stated, the conventional notation used herein for nucleic acids is as follows: the left-hand end of single-stranded nucleic acid is the 5' end; the left-hand direction of double-stranded nucleic acid is referred to as the 5' direction. The direction of 5' to 3' addition of nascent RNA transcripts is referred to as the transcription direction. Sequence regions on the DNA strand having the same sequence as the RNA and which are 5' to the 5' end of the RNA transcript are referred to as "upstream sequences;" sequence regions on the DNA strand having the same sequence as the RNA and which are 3' to the 3' end of the coding RNA transcript are referred to as "downstream sequences".

Nucleic acids include RNA, mRNA, cDNA, genomic DNA, synthetic forms, and mixed polymers, both sense and antisense strands, and can also be chemically or biochemically modified or can contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, and carbamates), charged linkages (e.g., phosphorothioates and phosphorodithioates), pendent moieties (e.g., polypeptides), intercalators (e.g., acridine and psoralen), chelators, alkylators, and modified linkages (e.g., alpha anomeric nucleic acids). Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule.

The terms "amino acid" or "amino acid residue", as used herein, refer to L amino acids or to D amino acids as described further below. The commonly used one- and three-letter abbreviations for amino acids are used herein (see, e.g., Alberts et al., Molecular Biology of the Cell, Garland Publishing, Inc., New York (3d ed. 1994)).

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, and the like) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), which is incorporated by reference herein.) In addition, individual substitutions, deletions or additions that alter, add or delete a single amino acid or a small percentage of amino acids in an encoded sequence are also "conservative substitutions."

The term "relaxin analog" refers to a modified relaxin polypeptide that increases or decreases the functional activity of the molecule or its interaction with a relaxin receptor.

The term "soluble," in the context of a polypeptide, refers to the ability of the polypeptide to be dissolved in (i.e., to be molecularly or ionically dispersed in) an aqueous solution, such as water, blood or plasma.

The term "small molecule effector," in the context of relaxin or a relaxin receptor, refers to an agent that binds to a relaxin, or to a relaxin receptor, and stimulates the activity of relaxin or relaxin receptor.

The term "small molecule antagonist," in the context of a relaxin or a relaxin receptor, refers to an agent that binds to a relaxin, or to a relaxin receptor, and reduces or inhibits the activity of relaxin or relaxin receptor.

The term "effective amount" means a dosage sufficient to provide amelioration of a symptom or treatment for an abnormality, such as a disease, disorder or condition, being treated. The dosage will vary depending on the subject, the abnormality being treated, and the treatment being effected.

The terms "subnormal," "subnormally" and "underdeveloped," in the context of body tissue and/or cells, refer to a smaller size, decreased cell number, and/or immature developmental state, as compared with the size, cell number and/or developmental state of a tissue and/or cells of a normal subject of the same age and species of the subject.

The term "tissue" refers to a population of cells, generally consisting of cells of the same kind that perform the same, or a similar, function. A tissue can be part of an organ or bone or it can be a loose association of cells, such as cells of the immune system.

The term "maturation," in the context of body tissue, refers to the developmental progression and/or differentiation of the tissue towards its full developed state.

The term "mature," in the context of body tissue, refers to the achievement of full development, differentiation and/or growth of the tissue.

The term "immature," in the context of body tissue, refers to a tissue that has not fully developed and/or differentiated.

The term "pre-pubescent male" refers to a male that has not completed the process of puberty.

The term "post-pubescent male" refers to a male that has completed the process of puberty.

The term "puberty" refers to the sequence of events by which a child becomes a young adult, characterized by the beginning of gametogenesis, secretion of gonadal hormones, development of secondary sexual characteristics, and reproductive function.

The term "accumulation," in the context of body tissue, refers to an increase in the number of normal (i.e., non-mutant, non-malignant) cells in the tissue.

The terms "biologically active" and "functionally active" refer to the ability of a molecule (e.g., a relaxin agonist or antagonist) to bind to a relaxin or relaxin receptor and to stimulate or inhibit apoptosis, cell accumulation/ and/or tissue maturation, in a body tissue.

The term "relaxin-deficient condition" refers to a disease, disorder or condition of a subject, in which relaxin levels, or relaxin-receptor levels, in the relevant tissue, cell(s), or in the subject, are below normal.

The term "relaxin-responsive" refers to an increase in cell number, or in the state of maturity (i.e., tissue development and/or differentiation), in response to the binding of relaxin to a relaxin receptor.

The term "relaxin-associated" refers to a property, condition or response of a cell or tissue by which the cell or tissue is affected, directly or indirectly, by an increase or decrease in functionally active relaxin levels, or in functionally active relaxin receptor.

The terms "hyperplasia" or "hyperplastic tissue" refer to an increase in the number of cells in a tissue.

The terms "hypertrophy" or "hypertrophic" refer to an increase in the size of a tissue.

The terms "cancer" and "malignancy" generally refer to the various types of malignant neoplasms, most of which invade surrounding tissues.

The terms "cancerous" and "malignant" relate to cells or tissue having properties of cancer or a malignancy.

The term "tissue remodeling" refers to the formation of new cells or tissues and the destruction of existing cells through the apoptotic pathway, in response to the signals mediated by relaxin or a relaxin-receptor.

The term "apoptosis" refers to a regulated network of biochemical events which lead to a selective form of cell suicide, and is characterized by readily observable morphological and biochemical phenomena, such as the fragmentation of the deoxyribonucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient.

DETAILED DESCRIPTION

The present invention provides methods for the administration of relaxin agonists or antagonists for the modulation of apoptosis. The relaxin agonists and antagonists can be used to reduce, manage, treat or prevent relaxin-associated abnormalities. Relaxin-associated abnormalities include diseases, disorder or conditions of a subject that are associated with increased or decreased levels of apoptosis, as compared with levels of apoptosis in a normal subject. Relaxin-associated abnormalities include, for example, relaxin-deficient conditions and relaxin-responsive conditions.

In one aspect, a relaxin agonist is administered to a subject to treat a relaxin-associated abnormality having increased apoptosis, as compared with comparable cells from a normal subject (i.e., not having the relaxin-associated abnormality). Such relaxin-associated abnormalities can include, for example, immature body tissue, increased collagen deposition, fibrosis (i.e., the presence of abnormal amounts of fibrous tissue, as compared with normal tissue), low tissue weight, increased apoptosis of cells in a cell population in a tissue, and the like. Relaxin-associated abnormalities are typically associated with decreased levels of relaxin, and/or relaxin receptor, as compared with normal cell or tissues.

In certain embodiments, the relaxin-associated abnormality is a relaxin-deficient condition, such as, for example, immature tissue, the presence of excessive collagen, a low sperm count, and the like. The immature tissue can be, for example, immature male productive tract tissue (e.g., immature prostatic, epididymal, seminiferous or testicular tissue or sperm). Immature tissue can be characterized, for example, by increased collagen deposition, low weight, and/or decreased cell number, as compared with a comparable sample of normal tissue. Such tissue also can be characterized by its lack of organization, by incomplete development and/or by a lack of, or incomplete, differentiation, as compared with a comparable sample of normal tissue. In certain other embodiments, fibrosis can be reduced, such as, for example, dermal fibrosis, lung fibrosis, kidney fibrosis, or age-related fibrosis of these or other organs or tissues.

The relaxin agonist is administered in an amount effective to reduce, manage, treat or prevent the relaxin-associated abnormality. For example, administration of a relaxin agonist can decrease apoptosis of target cells, stimulate maturation, development and/or differentiation of immature tissue, increase tissue weight, increase cell number in the tissue, decrease in collagen deposition, and the like.

In another aspect according to the present invention, a relaxin antagonist is administered to a subject to reduce, manage, treat or prevent a relaxin-associated abnormality by increasing apoptosis in the target cells. Such relaxin associated abnormalities can be, for example, relaxin-associated cell accumulation, decreased apoptosis relative to normal cells or tissue, hyperplasia, hypertrophy, cancer, neoplasia, and the like. In certain embodiments, the relaxin antagonist can reduce relaxin-associated tissue remodeling, reduce unwanted cell accumulation, reduce or prevent hyperplasia, hypertrophy, cancer, neoplasia, and the like.

Body tissues having relaxin-associated or relaxin-responsive tissue abnormalities can include, for example, tissues of the brain, heart, liver, kidney, spleen, thymus, intestine, skin, lung, male reproductive tract (e.g., prostate, epididymis, seminal vesicles or testes), or female reproductive tract (e.g., the uterus, cervix, the interpubic ligament or connective tissues of the pelvic girdle).

Relaxin Agonists

In one aspect according to the present invention, a relaxin agonist is administered to a subject to treat a relaxin-associated abnormality. The relaxin agonist can be, for example, a relaxin, a relaxin analog, a small molecule relaxin effector, a relaxin nucleic acid, and the like.

Relaxin and Relaxin Analogs

In one aspect of the invention, the relaxin agonist is a relaxin polypeptide or a fragment or analog of a relaxin polypeptide. The term "relaxin" refers to vertebrate relaxin polypeptides, including full length relaxin polypeptide or a portion of the relaxin polypeptide that retains biological activity.

Figure 1:
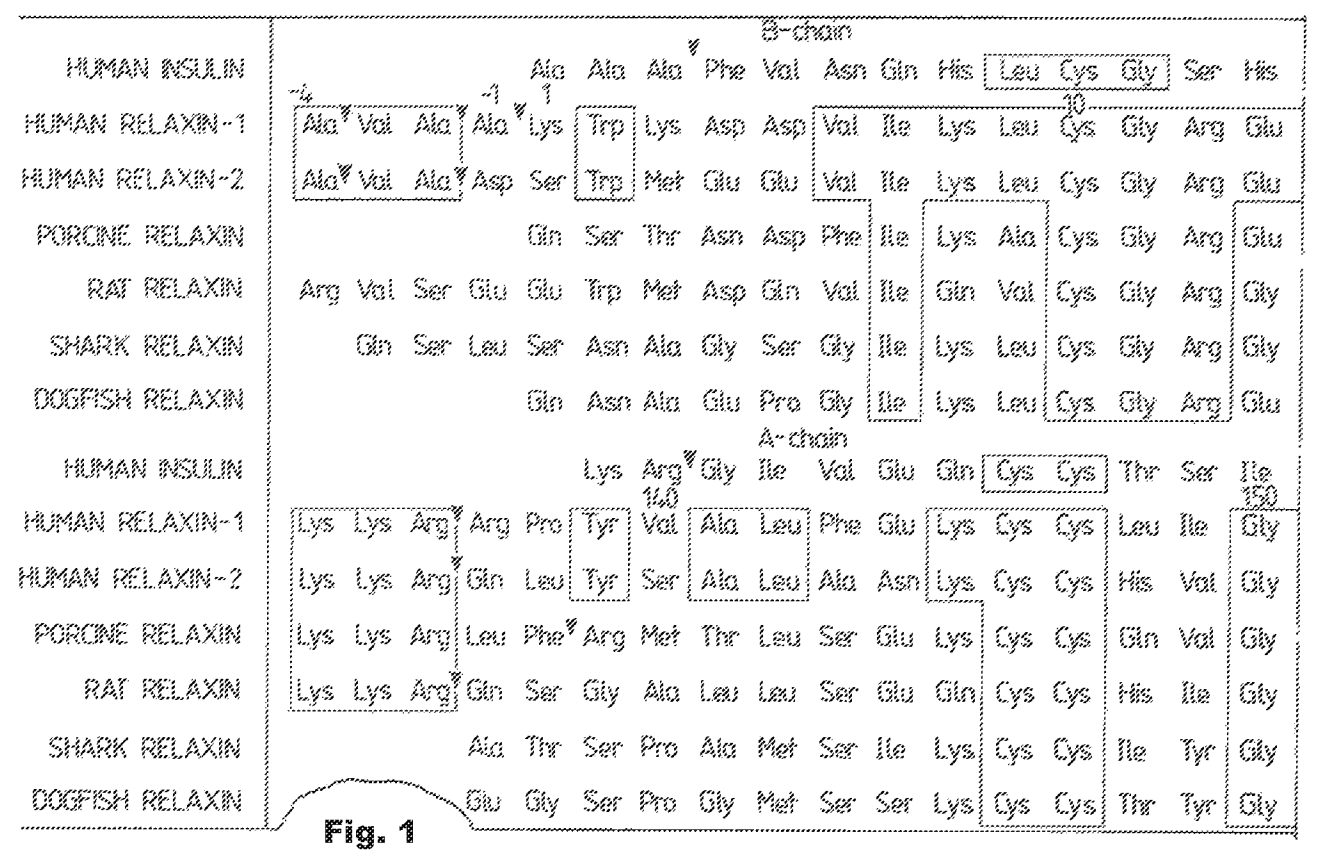

Relaxin has been well defined in its natural human form, animal form, and in its synthetic form. In particular, relaxin has been extensively described in U.S. Pat. Nos. 5,166,191; 5,023,251; and 4,835,251 (both of which are hereby incorporated by reference). In this application "relaxin" generally refers to the terms "relaxin," "human relaxin," "native relaxin," and "synthetic relaxin" as defined in U.S. Pat. No. 5,166,191 and the terms "human relaxin" and "human relaxin analogs" as defined in U.S. Pat. No. 4,835,251. In a typical embodiment, the relaxin, as described in, for example, U.S. Pat. Nos. 5,179,195; 5,023,195; and 4,758,516 (the disclosures of which are incorporated by reference herein). See FIG. 1. "Relaxin" in this application will also refer to relaxin as isolated from pigs, rats, horses, or other mammalian or vertebrates, and relaxin produced by recombinant techniques using cDNA clones for rat, porcine or other mammalian or vertebrate relaxin(s).

Methods of making relaxin and its analogs are known in the art. In addition, methods for isolating and purifying relaxin are known in the art. Several sources for these methods are identified in U.S. Pat. No. 5,166,191, including the following references: U.S. Pat. No. 4,835,251, Barany et al., The Peptides 2:1 (1980), Treager et al., Biology of Relaxin and its Role in the Human, pp. 42-55; EP 0 251 615; EP 0 107 782; EP 0 107 045; and WO 90/13659 (all of which are incorporated by reference herein).

Additional methods of making relaxin are described in U.S. Pat. No. 5,464,756, and PCT/US94/06997 (the disclosures of which are incorporated by reference herein). Relaxin can also be prepared by synthesis of the A and B chains, and purification and assembly thereof, as described in European Patent 0 251 615 (published Jan. 7, 1988, the disclosure of which is incorporated herein by reference). For in vitro assembly of relaxin, a 4:1 molar ratio of A to B chains is generally employed. The resulting product is then purified by any means known to one of ordinary skill in the art, including, for example, reverse-phase HPLC, ion exchange chromatography, gel filtration, dialysis, and the like, or any combination of such procedures. Unprocessed or partially processed forms of relaxin, such as preprorelaxin or prorelaxin, can also be used.

In specific embodiments, relaxin polypeptides include the H1 (chain B—SEQ ID NO:1 and chain A—SEQ ID NO:2) and H2 (chain B—SEQ ID NO:3 and chain A—SEQ ID NO:4) forms of human relaxin. It has been reported that the predominant species of human relaxin is the H2 form with a truncated B chain (i.e., relaxin H2(B29 (Amino acids 4 to 32 of SEQ ID NO:3) A24 (Amino acids 4 to 27 of SEQ ID NO:4))), wherein the four C-terminal amino acids of the B-chain (SEQ ID NO:3) are absent so that the B chain ends with a serine at position 32 of SEQ ID NO 3. Either form (referred to as designated "short relaxin" or "long relaxin," which contains a B chain of 33 amino acids) can be used.

Relaxin agonists further includes analogs, such as naturally-occurring amino acid sequence variants of relaxin. Relaxin analogs also include those altered by substitution, addition or deletion of one or more amino acid residues that provide for functionally active relaxin polypeptides. Such relaxin analogs include, but are not limited to, those containing as a primary amino acid sequence all or part of the amino acid sequence of a relaxin polypeptide, including altered sequences in which one or more functionally equivalent amino acid residues are substituted for residues within the sequence, resulting in a silent functional change (e.g., a conservative substitution).

In another aspect, the relaxin agonist is a polypeptide consisting of or comprising a fragment of a relaxin polypeptide having at least 10 contiguous amino acids of the relaxin polypeptide. Alternatively, the fragment contains at least 20 or 25 contiguous amino acids of the relaxin polypeptide. In other embodiments, the fragments are not larger than 20 or 30 amino acids.

The relaxin analog can be a polypeptide comprising regions that are substantially similar to a relaxin polypeptide or fragments thereof (e.g., in various embodiments, at least 60%, 70%, 75%, 80%, 90%, or even 95% identity or similarity over an amino acid sequence of identical size), or when compared to an aligned sequence in which the alignment is done by a computer sequence comparison/alignment program known in the art, or which coding nucleic acid is capable of hybridizing to a relaxin nucleic acid, under high stringency, moderate stringency, or low stringency conditions (infra). (See, e.g., Smith and Waterman, *Adv. Appl. Math.* 2:482 (1981); Needleman and Wunsch, *J. Mol. Biol.* 48:443 (1970); Pearson and Lipman, *Proc. Natl. Acad. Sci. USA* 85:2444 (1988); GAP, BESTFIT, FASTA, and TEASTA in the Wisconsin Genetics Software Package, Genetics Computer Group, 575 Science Dr., Madison, Wis.); Ausubel et al. (eds.), *Current Protocols in Molecular Biology*, 4th ed., John Wiley and Sons, New York (1999); the disclosures of which are incorporated by reference herein). Relaxin agonists further comprise functionally active relaxin polypeptides, analogs or fragments that bind to a relaxin receptor.

Relaxin agonists, such as relaxin polypeptides, analogs and fragments can be produced by various methods known in the art. The manipulations which result in their production can occur at the gene or polypeptide level. For example, cloned relaxin nucleic acids can be modified by any of numerous strategies known in the art (see, e.g., Sambrook et al., *Molecular Cloning: A Laboratory Manual*, 3d Ed., Cold Spring Harbor Laboratory Press, New York (2001); Ausubel et al., *Current Protocols in Molecular Biology*, 4th ed., John Wiley and Sons, New York (1999); which are incorporated by reference herein), such as making conservative substitutions, deletions, insertions, and the like. The sequence can be cleaved at appropriate sites with restriction endonuclease(s), followed by further enzymatic modification if desired, isolated, and ligated in vitro. In the production of the relaxin nucleic acids encoding an analog or fragment, the modified nucleic acid typically remains in the proper translational reading frame, so that the reading frame is not interrupted by translational stop signals or other signals that interfere with the synthesis of the relaxin analog or fragment. The relaxin nucleic acid can also be mutated in vitro or in vivo to create and/or destroy translation initiation and/or termination sequences. The relaxin nucleic acid can also be mutated to create variations in coding regions and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (see, e.g., Hutchison et al., *J. Biol. Chem.* 253:6551-60 (1978)), the use of TAB® linkers (Pharmacia), and the like. (See generally Sambrook et al., supra; Ausubel et al., supra.)

In a specific embodiment, relaxin analogs are prepared from relaxin-encoding nucleic acids that are altered to introduce aspartic acid codons at specific position(s) within at least a portion of the relaxin coding region. (See, e.g., U.S. Pat. No. 5,945,402, the disclosure of which is incorporated by reference herein.) The resulting analogs can be treated with dilute acid to release a desired analog, thereby rendering the protein more readily isolated and purified. Other relaxin analogs are disclosed in U.S. Pat. Nos. 4,656,249; 5,179,195; 5,945,402; 5,811,395; and 5,795,807 (the disclosures of which are incorporated by reference herein).

Manipulations of the relaxin polypeptide sequence can also be made at the polypeptide level. Included within the scope of the invention are relaxin polypeptides, analogs or fragments that are differentially modified during or after synthesis (e.g., in vivo or by in vitro translation). Such modifications include conservative substitution, glycosylation, acetylation, phosphorylation, amidation, derivatization by known protecting/blocking groups, proteolytic cleavage, linkage to an antibody molecule, another polypeptide or other cellular ligand, and the like. Any of numerous chemical modifications can be carried out by known techniques, including, but not limited to, specific chemical cleavage (e.g., by cyanogen bromide), enzymatic cleavage (e.g., by trypsin, chymotrypsin, papain, V8 protease, and the like); modification by, for example, NaBH$_4$, acetylation, formylation, oxidation and reduction, metabolic synthesis in the presence of tunicamycin, and the like.

Relaxin polypeptides, analogs and fragments can be purified from natural sources by standard methods such as those described herein (e.g., immunoaffinity purification). Relaxin polypeptides, analogs and fragments can also be isolated and purified by standard methods including chromatography (e.g., ion exchange, affinity, sizing column chromatography, high pressure liquid chromatography), centrifugation, differential solubility, or by any other standard technique for the purification of polypeptides. Relaxin polypeptides can be synthesized by standard chemical methods known in the art (see, e.g., Hunkapiller et al., *Nature* 310:105-11 (1984); Stewart and Young, *Solid Phase Peptide Synthesis*, $2^{nd}$ Ed., Pierce Chemical Co., Rockford, Ill., (1984); the disclosures of which are incorporated by reference herein).

In addition, analogs of relaxin polypeptides can be chemically synthesized. For example, a peptide corresponding to a fragment of a relaxin polypeptide, which comprises a desired domain, or which mediates a desired activity in vivo, can be synthesized by use of chemical synthetic methods using, for example, an automated peptide synthesizer. Furthermore, if desired, nonclassical amino acids or chemical amino acid analogs can be introduced as a substitution or addition into the relaxin polypeptide sequence. Non-classical amino acids include, but are not limited to, the D-isomers of the common amino acids, α-amino isobutyric acid, 4-aminobutyric acid, 2-amino butyric acid, ε-amino hexanoic acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In another embodiment, the relaxin agonist is a chimeric, or fusion, protein comprising a relaxin polypeptide, or fragment thereof (typically consisting of at least a domain or motif of the relaxin polypeptide, or at least 10 contiguous amino acids of the relaxin polypeptide, joined at its amino- or carboxy-terminus via a peptide bond to an amino acid sequence of a different protein. In one embodiment, such a chimeric protein is produced by recombinant expression of a nucleic acid encoding the chimeric polypeptide. The chimeric product can be made by ligating the appropriate nucleic acid sequences, encoding the desired amino acid sequences, to each other in the proper reading frame and expressing the chimeric product by methods commonly known in the art. Alternatively, the chimeric product can be made by protein synthetic techniques (e.g., by use of an automated peptide synthesizer).

In a specific embodiment, the fusion protein is a relaxin-ubiquitin fusion protein. For example, U.S. Pat. No. 5,108,919 (the disclosure of which is incorporated herein by reference) discloses methods for preparing a fusion protein of a relaxin chain and ubiquitin.

In preferred embodiments, the relaxin analog, or fragment is functionally active (i.e., capable of exhibiting one or more functional activities associated with a full-length, wild-type relaxin polypeptide). As one example, analogs or fragments that retain a desired relaxin property of interest (e.g., binding to a relaxin binding partner (e.g., relaxin receptor) and/or modulation (e.g., inhibition) of apoptosis) can be used as inducers of such property and its physiological correlates. A specific embodiment relates to a relaxin analog or fragment that bind to a relaxin receptor and induces a relaxin-associated decrease in apoptosis. Analogs or fragments of relaxin can be tested for the desired activity by procedures known in the art, including but not limited to the functional assays described herein.

Relaxin Nucleic Acids:

The invention provides relaxin nucleic acid sequences for expression of relaxin polypeptide, fragments and analogs in vivo or in vitro. The relaxin nucleic acid can be a vertebrate or mammalian relaxin, including, for example, human, mouse, rat, pig, cow, dog, or monkey relaxin. The relaxin nucleic acids can comprise genomic nucleic acids, cDNA, the relaxin coding region or a fragment thereof. Relaxin nucleic acids further include mRNAs corresponding to the relaxin locus. Relaxin nucleic acids can also include analogs (e.g., nucleotide sequence variants), such as those encoding other possible codon choices for the same amino acid or conservative amino acid substitutions thereof, such as naturally occurring allelic variants. Due to the degeneracy of nucleotide coding sequences, other nucleic acid sequences that encode substantially the same amino acid sequence as a relaxin cDNA or open reading frame, can be used in the practice of the present invention. These nucleic acid sequences include, but are not limited to, nucleic acid sequences comprising all or portions of a relaxin gene which is altered by the substitution of different codons that encode the same or a functionally equivalent amino acid residue (e.g., a conservative substitution) within the sequence, thus producing a silent change.

The invention further provides relaxin nucleic acid fragments of at least 6 contiguous nucleotides (e.g., a hybridizable portion); in other embodiments, the nucleic acids comprise at least 8 contiguous nucleotides, at least contiguous 25 nucleotides, at least contiguous 50 nucleotides, at least 100 nucleotides, or at least, 150 nucleotides, or more of a relaxin sequence. In another embodiment, the nucleic acids are smaller than 150 nucleotides in length. The relaxin nucleic acids can be single or double-stranded. As is readily apparent, as used herein, a "nucleic acid encoding a fragment of a relaxin polypeptide" is construed as referring to a nucleic acid encoding only the recited fragment or portion of the relaxin polypeptide and not the other contiguous portions of the relaxin polypeptide as a contiguous sequence. Fragments of relaxin nucleic acids encoding one or more relaxin domains are also provided.

Relaxin nucleic acids, or a functionally active analog or fragment thereof, can be inserted into an appropriate vector, such as an expression vector (i.e., a vector which contains the necessary elements for the transcription and translation of the inserted polypeptide-coding sequence). The necessary transcriptional and translational signals can also be supplied by the native relaxin gene and/or its flanking regions. A variety of host-vector systems can be utilized to express the relaxin nucleic acid sequences. These include but are not limited to, mammalian cell systems infected with virus (e.g., vaccinia virus, adenovirus, adeno-associated virus, and the like), insect cell systems infected with virus (e.g., baculovirus), microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements can be used.

In specific embodiments, human relaxin nucleic acids, or a nucleic acid sequence encoding a functionally active portion of human relaxin, is expressed in yeast or bacteria. In yet another embodiment, a fragment of relaxin comprising a domain of the relaxin polypeptide is expressed.

Any of the methods known in the art for the insertion of nucleic acids into a vector can be used to construct expression vectors containing a chimeric gene consisting of appropriate transcriptional/translational control signals and relaxin nucleic acid sequences. These methods include in vitro recombinant DNA and synthetic techniques and in vivo recombinants (genetic recombination). Expression of nucleic acid sequence encoding a relaxin polypeptide, analog or fragment can be regulated by a second nucleic acid sequence so that the relaxin polypeptide, analog or fragment is expressed in a host transformed with the recombinant DNA molecule. For example, expression of a relaxin polypeptide can be controlled by any promoter/enhancer element known in the art. Promoters which can be used to control relaxin gene expression include, but are not limited to, the SV40 early promoter region (Benoist and Chambon, *Nature* 290:304-10 (1981)), the promoter contained in the 3' long terminal repeat of Rous sarcoma virus (Yamamoto et al., *Cell* 22:787-97 (1980)), the herpes thymidine kinase promoter (Wagner et al., *Proc. Natl. Acad. Sci. USA* 78:1441-45 (1981)), the regulatory sequences of the metallothionen gene (Brinster et al., *Nature* 296:39-42 (1982)), prokaryotic expression vectors such as the β-lactamase promoter (Villa-Komaroff et al., *Proc. Natl. Acad. Sci. USA* 75:3727-31 (1978)) or the tac promoter (deBoer et al., *Proc. Natl. Acad. Sci. USA* 80:21-25 (1983)), plant expression vectors including the cauliflower mosaic virus 35S RNA promoter (Gardner et al., *Nucl. Acids Res.* 9:2871-88 (1981)), the promoter of the photosynthetic enzyme ribulose biphosphate carboxylase (Herrera-Estrella et al., *Nature* 310:115-20 (1984)), promoter elements from yeast or other fungi such as the Gal7 and Gal4 promoters, the ADH (alcohol dehydrogenase) promoter, the PGK (phosphoglycerol kinase) promoter, the alkaline phosphatase promoter, and the like.

The following animal transcriptional control regions, which exhibit tissue specificity, have been utilized in transgenic animals: the elastase I gene control region which is active in pancreatic acinar cells (e.g., Swift et al., *Cell* 38:639-46 (1984); Ornitz et al., *Cold Spring Harbor Symp. Quant. Biol.* 50:399-409 (1986); MacDonald, *Hepatology* 7(1 Suppl.):42S-51S (1987)); the insulin gene control region which is active in pancreatic beta cells (e.g., Hanahan, *Nature* 315:115-22 (1985)), the immunoglobulin gene control region which is active in lymphoid cells (e.g., Grosschedl et al., *Cell* 38:647-58 (1984); Adams et al., *Nature* 318:533-38 (1985); Alexander et al., *Mol. Cell. Biol.* 7:1436-44 (1987)), the mouse mammary tumor virus control region which is active in testicular, breast, lymphoid and mast cells (e.g., Leder et al., *Cell* 45:485-95 (1986)), the albumin gene control region which is active in liver (e.g., Pinkert et al., *Genes Dev.* 1:268-76 (1987)), the alpha-fetoprotein gene control region which is active in liver (e.g., Krumlauf et al., *Mol. Cell. Biol.* 5:1639-48 (1985); Hammer et al., *Science* 235:53-58 (1987)); the alpha 1-antitrypsin gene control region which is active in the liver (e.g., Kelsey et al., *Genes and Devel.* 1:161-71 (1987)); the beta-globin gene control region which is active in myeloid cells (e.g., Magram et al., *Nature* 315:338-40 (1985); Kollias et al., *Cell* 46:89-94 (1986)); the myelin basic protein gene control region which is active in oligodendrocyte cells in the brain (e.g., Readhead et al., *Cell* 48:703-12 (1987)), the myosin light chain-2 gene control region which is active in skeletal muscle (e.g., Shani, *Nature* 314:283-86 (1985)); and the gonadotropic releasing hormone gene control region which is active in the hypothalamus (e.g., Mason et al., *Science* 234:1372-78 (1986)). In a preferred embodiment, the tissue specific promoter is the prostate specific antigen promoter. (See, e.g., U.S. Pat. No. 6,100,444, the disclosure of which is incorporated by reference herein.)

In another embodiment, a vector is used that comprises a promoter operably linked to a relaxin nucleic acid, one or more origins of replication, and, optionally, one or more selectable markers (e.g., an antibiotic or drug resistance marker). For example, an expression construct can be made by subcloning a relaxin nucleic acid into a restriction site of the pRSECT expression vector. Such a construct allows for the expression of a relaxin polypeptide, analog or fragment under the control of the T7 promoter with a histidine amino terminal flag sequence for affinity purification of the expressed polypeptide. In another specific embodiment, a vector is used that comprises the prostate specific antigen promoter operably linked to a relaxin nucleic acid, one or more origins of replication, and, optionally, one or more selectable markers (e.g., an drug resistance marker).

Expression vectors containing relaxin nucleic acids can be identified by general approaches well known to the skilled artisan, including: (a) nucleic acid hybridization, (b) the presence or absence of "marker" gene function, (c) expression of inserted sequences, (d) by polymerase chain reaction (PCR), and the like. In the first approach, the presence of a relaxin nucleic acid inserted in an expression vector can be detected by nucleic acid hybridization using probes comprising sequences that are homologous to an inserted relaxin nucleic acid. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, colorimetric change, and the like) caused by the insertion of the relaxin nucleic acids into the vector. For example, if the relaxin nucleic acid is inserted within the marker gene sequence of the vector, recombinants containing the relaxin nucleic acid can be identified by the absence of the marker gene function.

In the third approach, recombinant expression vectors can be identified by assaying the relaxin polypeptide, analog or fragment expressed by the recombinant. Such assays can be based, for example, on the physical or functional properties of the relaxin polypeptide, analog or fragment in in vitro assay systems (e.g., binding with anti-relaxin antibody, binding to relaxin receptor, and the like). In a forth approach, recombinant expression vectors can be identified by polymerase chain reaction. (See, e.g., U.S. Pat. Nos. 4,683,202, 4,683,195 and 4,889,818; Gyllensten et al., *Proc. Natl. Acad. Sci. USA* 85:7652-56 (1988); Ochman et al., *Genetics* 120:621-23 (1988); Loh et al., *Science* 243:217-20 (1989).) Once a particular recombinant vector is identified and isolated, several methods that are known in the art can be used to propagate it.

Once a suitable host system and growth conditions are established, recombinant vectors can be propagated and prepared in quantity. As previously explained, the vectors which can be used include, but are not limited to the following vectors or their analogs: human or animal viruses such as vaccinia virus or adenovirus; insect viruses such as baculovirus; yeast vectors; bacteriophage vectors (e.g., lambda); and plasmid and cosmid DNA vectors; to name but a few.

In addition, a host cell strain can be chosen that modulates the expression of the inserted nucleic acids, or modifies or processes the relaxin, relaxin analog or fragment in the specific fashion desired. Expression from certain promoters can be elevated in the presence of certain inducers; thus, expression of the relaxin polypeptide, analog or fragment can be controlled. Furthermore, different host cells having characteristic and specific mechanisms for the translational and post-translational processing, and modification (e.g., glycosylation and/or phosphorylation) can be used. Appropriate cell lines or host systems can be chosen to ensure the desired modification and processing of the polypeptide, analog or fragment expressed. For example, expression in a bacterial system can be used to produce an unprocessed core protein product. Expression in mammalian cells can be used to ensure "native" processing of mammalian relaxin polypeptides, or of analogs or fragments. Furthermore, different vector/host expression systems can affect processing reactions to different extents.

Relaxin Antagonists

In another aspect of the invention, relaxin antagonists are provided for the modulation of apoptosis. Relaxin antagonists can include, for example, relaxin binding agents, relaxin receptor binding agents, antisense nucleic acids, and the like.

Relaxin Antibodies

Relaxin antagonists can comprise antibodies that immunospecifically-recognize relaxin or a relaxin receptor polypeptide and that stimulate apoptosis, and/or reduce or inhibit relaxin-associated cell accumulation in cell populations or tissues. Anti-relaxin and anti-relaxin receptor antibodies include, but are not limited to, polyclonal antibodies, monoclonal antibodies, chimeric antibodies (e.g., fully humanized antibodies or human chimeric antibodies), single chain antibodies, antibody fragments (e.g., Fab, F(ab'), F(ab')$_2$, Fv, or hypervariable regions), single heavy chains, and an Fab expression library. In a specific embodiment, polyclonal and/or monoclonal antibodies to full length, vertebrate or mammalian relaxin or relaxin receptor polypeptide are produced and selected for those antibodies that selectively bind to relaxin or a relaxin receptor polypeptides, and thereby functionally inactivate such polypeptides. In another embodiment, antibodies to a domain of a vertebrate relaxin polypeptide, or a relaxin receptor polypeptide, are produced. In still another embodiment, fragments of a vertebrate relaxin polypeptide, or a relaxin receptor polypeptide, which are identified as hydrophilic, are used as immunogens for antibody production and selected for immunospecific binding to such a polypeptide and inhibition of its biological activity.

Various procedures known in the art can be used for the production of polyclonal antibodies to a relaxin or relaxin receptor polypeptide, or a fragment or analog thereof. For the production of such antibodies, various host animals (including, but not limited to, rabbits, mice, rats, sheep, goats, and the like) can be immunized by injection with the native relaxin or relaxin receptor polypeptide, or a fragment or analog thereof. Alternatively, transgenic animals having a human immune system can be immunized by injection with the native relaxin or relaxin receptor polypeptide. (See, e.g., U.S. Pat. Nos. 6,114,598 and 6,111,166, which are incorporated by reference herein.) Various adjuvants can be used to increase the immunological response, depending on the host species, including but not limited to Freund's adjuvant (complete or incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a relaxin or relaxin receptor polypeptide, fragment, or analog thereof, any technique which provides for the production of antibody molecules by continuous cell lines in culture can also be used. Such techniques include, for example, the hybridoma technique originally developed by Kohler and Milstein (*Nature* 256:495-97 (1975)), as well as the trioma technique, the human B-cell hybridoma technique (see, e.g., Kozbor et al., *Immunology Today* 4:72 (1983)), and the EBV-hybridoma technique to produce human monoclonal antibodies (see, e.g., Cole et al., In *Monoclonal Antibodies and Cancer Therapy*, Alan R. Liss, Inc., pp. 77-96 (1985)). Mammalian antibodies can be used and can be obtained by using hybridomas (see, e.g., Cote et al., *Proc. Natl. Acad. Sci. USA* 80:2026-30 (1983)) or by transforming human B cells with EBV virus in vitro (see, e.g., Cole et al. (1985), supra). Selection of hybridomas producing antibodies with appropriate biological function are well known in the art or are described herein below. Human monoclonal antibodies can also be prepared by preparing hybridomas from animals having a human immune system that have been immunized by injection with the native relaxin or relaxin receptor polypeptide. (See, e.g., U.S. Pat. No. 6,114,598 and U.S. Pat. No. 6,111,166, which are incorporated by reference herein.)

Further to the invention, "chimeric" or "humanized" antibodies (see, e.g., Morrison et al., *Proc. Natl. Acad. Sci. USA* 81:6851-55 (1984); Neuberger et al., *Nature* 312:604-08 (1984); Takeda et al., *Nature* 314:452-54 (1985)) can be prepared. Such chimeric antibodies are typically prepared by splicing the non-human genes for an antibody molecule specific for a relaxin or receptor polypeptide together with genes from a human antibody molecule of appropriate activity. It can be desirable to transfer the antigen binding regions (e.g., an F(ab')$_2$, F(ab'), Fv, or hypervariable region(s)) of non-human antibodies into the framework of a human antibody by recombinant DNA techniques to produce a substantially human molecule. In a preferred embodiment, the antibodies are fully humanized.

Methods for producing such "chimeric" molecules are generally well known and described in, for example, U.S. Pat. Nos. 4,816,567; 4,816,397; 5,693,762; 5,712,120; 5,821,337; 6,054,297; International Patent Publications WO 87/02671 and WO 90/00616; and European Patent Publication EP 0 239 400 (the disclosures of which are incorporated by reference herein). Alternatively, a human monoclonal antibody or portions thereof can be identified by first screening a human B-cell cDNA library for DNA molecules that encode antibodies that specifically bind to a relaxin or a relaxin receptor polypeptide according to the method generally set forth by Huse et al. (*Science* 246:1275-81 (1989)). The DNA molecule can then be cloned and amplified to obtain sequences that encode the antibody (or binding domain) of the desired specificity. Phage display technology offers another technique for selecting antibodies that bind to relaxin or relaxin receptor polypeptides, fragments or analogs thereof. (See, e.g., International Patent Publications WO 91/17271 and WO 92/01047; and Huse et al., supra.)

According to another aspect of the invention, techniques for the production of single chain antibodies (see, e.g., U.S. Pat. Nos. 4,946,778 and 5,969,108) can be adapted to produce relaxin- or relaxin receptor-specific single chain antibodies. (See also Riechmann and Muyldermans, *J. Immunol. Methods* 231:25-38 (1999); Muyldermans and Lauwereys, *J. Mol. Recognit.* 12:131-40 (1999)).

An additional aspect of the invention utilizes the techniques described for the construction of a Fab expression library (see, e.g., Huse et al. (1989), supra) to allow rapid and easy identification of monoclonal Fab fragments with the desired specificity for relaxin polypeptides, fragments, or analogs thereof and biological activity.

Antibody fragments which contain the idiotype of the molecule can be generated by known techniques. For example, such fragments include, but are not limited to, an F(ab')$_2$ fragment which can be produced by pepsin digestion of the antibody molecule, Fab' fragments which can be generated by reducing the disulfide bridges of the F(ab')$_2$ fragment, Fab fragments which can be generated by treating the antibody molecule with papain and a reducing agent, and Fv fragments. Recombinant Fv fragments can also be produced in eukaryotic cells using, for example, the methods described in U.S. Pat. No. 5,965,405.

In the production of antibodies, screening for the desired antibody can be accomplished by techniques known in the art (e.g., ELISA (enzyme-linked immunosorbent assay)). In one example, antibodies which recognize a specific domain of a relaxin or relaxin receptor polypeptide can be used to assay hybridomas for a product (e.g., antibody) that binds to a relaxin or relaxin receptor fragment containing that domain. For selection of an antibody that specifically binds to a first relaxin or relaxin receptor polypeptide, but which does not specifically bind a second, different relaxin polypeptide, one can select on the basis of antibody-positive binding to the first polypeptide and a lack of antibody binding to the second, different polypeptide.

Soluble Relaxin Receptors

In another aspect of the invention, the relaxin antagonist is a relaxin binding agent comprising a soluble relaxin receptor, or a fragment or analog thereof, that binds relaxin. The term "soluble relaxin receptor" refers to a relaxin receptor polypeptide that is not bound to a cell membrane. The relaxin receptor is approximately 200 kilodaltons. (See Palejwala et al., *Endocrinology* 139(3):1208-12 (1998), the disclosure of which is incorporated by reference herein.) The soluble form of the relaxin receptor retains the ability to bind vertebrate relaxin, but typically lacks transmembrane and/or cytoplasmic domains. Soluble relaxin receptors can comprise additional amino acid residues, such as affinity tags, that provide for a means for purification of the polypeptide or to provide sites for attachment of the polypeptide to another polypeptide, or to immunoglobulin sequences.

The soluble relaxin receptor can optionally contain a transmembrane domain that cannot associate with a cell membrane. By "transmembrane domain" is meant a domain of the relaxin receptor polypeptide that contains a sufficient number of hydrophobic amino acids to allow the polypeptide to insert and anchor in a cell membrane. By "transmembrane domain that cannot associate with a cell membrane" is meant a transmembrane domain that has been altered by mutation or deletion such that it is not sufficiently hydrophobic to allow insertion or other association with a cell membrane. Such a transmembrane domain does not preclude, for example, the fusion of the relaxin receptor polypeptide, or fragment thereof, with a secretion signal sequence useful for secretion of the polypeptide from the cell. Substitutions or alterations of the amino acid sequence useful to achieve an inactive transmembrane domain include, but are not limited to, deletion or substitution of amino acids within the transmembrane domain. Methods of making soluble receptors are known in the art. (See, e.g., U.S. Pat. Nos. 6,033,903; 6,037,450; and 5,925,549; the disclosures of which are incorporated by reference herein.)

The soluble relaxin receptors include soluble, naturally-occurring amino acid sequence variants of relaxin receptor. Soluble relaxin receptors further include those altered by substitution, addition or deletion of one or more amino acid residues that provide for functionally active relaxin receptor polypeptides. Such relaxin receptors include, but are not limited to, those containing as a primary amino acid sequence of all or part of the amino acid sequence of a relaxin receptor polypeptide including sequences in which one or more functionally equivalent amino acid residues are substituted for residues within the sequence, resulting in a silent functional change (e.g., a conservative substitution).

In another aspect, the soluble relaxin receptor is a polypeptide consisting of or comprising a fragment of a relaxin receptor polypeptide having at least 10 contiguous amino acids of the relaxin receptor polypeptide. More typically, the fragment contains at least 20 or at least 50 contiguous amino acids of the relaxin receptor polypeptide. In other embodiments, the fragments are larger than 100 or even 200 amino acids.

The relaxin receptor polypeptide can be a polypeptide comprising regions that are substantially similar to a relaxin receptor polypeptide or fragments thereof (e.g., in various embodiments, at least 60%, 70%, 75%, 80%, 90%, or even 95% identity or similarity over an amino acid sequence of identical size), or when compared to an aligned sequence in which the alignment is done by a computer sequence comparison/alignment program known in the art, or by visual inspection. (See, e.g., Smith and Waterman, *Adv. Appl. Math.* 2:482 (1981); Needleman and Wunsch, *J. Mol. Biol.* 48:443 (1970); Pearson and Lipman, *Proc. Natl. Acad. Sci. USA* 85:2444 (1988); GAP, BESTFIT, FASTA, and TEASTA in the Wisconsin Genetics Software Package, Genetics Computer Group, 575 Science Dr., Madison, Wis.); Ausubel et al. (supra); the disclosures of which are incorporated by reference herein). Sequence identity or similarity can also be determined by identifying nucleic acids that are capable of hybridizing to a relaxin receptor nucleic acid, under high stringency, moderate stringency, or low stringency conditions. (See, e.g., Sambrook et al., *Molecular Cloning: A Laboratory Manual*, 3d Ed., Cold Spring Harbor Laboratory Press, New York (2001); Ausubel et al., (1996), supra; the disclosures of which are incorporated by reference herein).

Soluble relaxin receptors and fragments thereof can be produced by various methods known in the art. The manipulations which result in their production can occur at the gene or protein level. For example, cloned relaxin receptor nucleic acids can be modified by any of numerous strategies known in the art (see, e.g., Sambrook et al., supra; Ausubel et al., supra), such as making conservative substitutions, deletions, insertions, and the like. The sequence can be cleaved at appropriate sites with restriction endonuclease(s), followed by further enzymatic modification if desired, isolated, and ligated in vitro. In the production of the relaxin receptor nucleic acids, the modified nucleic acid typically remains in the proper translational reading frame, so that the reading frame is not interrupted by translational stop signals or other signals which interfere with the synthesis of the soluble relaxin receptor or fragment thereof. The relaxin receptor nucleic acid can also be mutated in vitro or in vivo to create and/or destroy translation initiation and/or termination sequences. The relaxin receptor nucleic acid can also be mutated to create variations in coding regions (e.g., amino acid substitutions) and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (see, e.g., Hutchison et al., *J. Biol. Chem.* 253:6551-60 (1978)), the use of TAB® linkers (Pharmacia), and the like.

Manipulations of the relaxin receptor polypeptide sequence can also be made at the polypeptide level. Included within the scope of the invention are relaxin receptor polypeptides that are differentially modified during or after synthesis (e.g., in vivo or by in vitro translation). Such modifications include conservative substitution, glycosylation, acetylation, phosphorylation, amidation, derivatization by known protecting/blocking groups, proteolytic cleavage, linkage to an antibody molecule, a protein or other cellular ligand, and the like. Any of numerous chemical modifications can be carried out by known techniques, including, but not limited to, specific chemical cleavage (e.g., by cyanogen bromide), enzymatic cleavage (e.g., by trypsin, chymotrypsin, papain, V8 protease, and the like); modification by, for example, $NaBH_4$, acetylation, formylation, oxidation and reduction, metabolic synthesis in the presence of tunicamycin, and the like.

Relaxin receptor polypeptides and fragments thereof can be purified from natural sources by standard methods such as those described herein (e.g., immunoaffinity purification). Relaxin receptor polypeptides and fragments can also be isolated and purified by standard methods including chromatography (e.g., ion exchange, affinity, sizing column chromatography, high pressure liquid chromatography), centrifugation, differential solubility, or by any other standard technique for the purification of polypeptides. Relaxin receptor polypeptides and fragments thereof can be synthesized by standard chemical methods known in the art (see, e.g., Hunkapiller et al., *Nature* 310:105-11 (1984); Stewart and Young, *Solid Phase Peptide Synthesis*, $2^{nd}$ Ed., Pierce Chemical Co., Rockford, Ill., (1984)). Furthermore, if desired, nonclassical amino acids or chemical amino acid analogs can be introduced as a substitution or addition into the relaxin receptor polypeptide sequence. Non-classical amino acids include, but are not limited to, the D-isomers of the common amino acids, α-amino isobutyric acid, 4-aminobutyric acid, 2-amino butyric acid, ε-amino hexanoic acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, α-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In another embodiment, the soluble relaxin receptor is a chimeric, or fusion, protein comprising a relaxin receptor polypeptide, or fragment thereof (typically consisting of at least a domain or motif of the relaxin receptor polypeptide, or at least 10 contiguous amino acids of the relaxin receptor polypeptide) joined at its amino- or carboxy-terminus via a peptide bond to an amino acid sequence of a different protein. In one embodiment, such a chimeric protein is produced by recombinant expression of a nucleic acid encoding the chimeric polypeptide. The chimeric product can be made by ligating the appropriate nucleic acid sequences, encoding the desired amino acid sequences, to each other in the proper reading frame and expressing the chimeric product by methods commonly known in the art. Alternatively, the chimeric product can be made by protein synthetic techniques (e.g., by use of an automated peptide synthesizer). In a specific embodiment, the fusion protein is a relaxin-receptor-ubiquitin fusion protein.

Relaxin Analogs

The relaxin antagonist can further be a relaxin analog, such as a relaxin polypeptide that binds to a relaxin receptor but fails to induce a response by that receptor. For example, the relaxin analog can be a competitive inhibitor of relaxin binding or a conventional antagonist of the relaxin receptor. The term "relaxin" refers to vertebrate relaxin polypeptides, including full length relaxin polypeptide or a portion of the relaxin polypeptide that retains biological activity. Relaxin has been well defined in its natural human form, animal form, and in its synthetic form. In particular, relaxin has been extensively described in U.S. Pat. Nos. 5,179,195; 5,166,191; 5,023,321; 4,835,251; and 4,758,516 (the disclosures of which are hereby incorporated by reference). Methods of making relaxin and its analogs are known in the art (supra). Relaxin analogs can be prepared by modification of relaxin polypeptides such that the relaxin analog retains relaxin receptor binding activity, but does not induce a response by the relaxin receptor. For example, relaxin analogs can be amino acid sequence variants of relaxin that retain relaxin receptor binding activity, but that fail to induce a response by a relaxin receptor. Relaxin analogs further include relaxin polypeptides, altered by addition or deletion of one or more amino acid residues, that retain receptor-binding function but fail to induce a response by relaxin receptor.

In various aspects according to the present invention, the relaxin analog is fragment of a relaxin polypeptide consisting of or comprising at least 10 contiguous amino acids of the relaxin polypeptide. Alternatively, the fragment contains at least 20 or 40 contiguous amino acids of the relaxin polypeptide. In other embodiments, the fragments are not larger than 35 amino acids.

The relaxin analog can be a polypeptide comprising regions that are substantially similar to a relaxin polypeptide (e.g., in various embodiments, at least 60%, 70%, 75%, 80%, 90%, or even 95% identity or similarity over an amino acid sequence of identical size), or when compared to an aligned sequence in which the alignment is done by a computer sequence comparison/alignment program known in the art, or which coding nucleic acid is capable of hybridizing to a relaxin nucleic acid, under high stringency, moderate stringency, or low stringency conditions. (See supra.)

Relaxin analogs can be produced by various methods known in the art. The manipulations which result in their production can occur at the gene or protein level. For example, cloned relaxin nucleic acids can be modified by any of numerous strategies known in the art (see, e.g., Sambrook et al., supra; Ausubel et al., supra), such as by making conservative or non-conservative substitutions, deletions, insertions, and the like. The sequence can be cleaved at appropriate sites with restriction endonuclease(s), followed by further enzymatic modification, if desired, isolated, and ligated in vitro. In the production of the relaxin analog nucleic acids, the modified nucleic acid typically remains in the proper translational reading frame, so that the reading frame is not interrupted by translational stop signals or other signals which interfere with the synthesis of the relaxin analog. The relaxin nucleic acid can be mutated in vitro or in vivo to create and/or destroy translation, initiation and/or termination sequences. The relaxin nucleic acid can also be mutated to create variations in coding regions and/or to form new restriction endonuclease sites or destroy pre-existing ones and to facilitate further in vitro modification.

Any technique for mutagenesis known in the art can be used, including but not limited to, chemical mutagenesis, in vitro site-directed mutagenesis (see, e.g., Hutchison et al., *J. Biol. Chem.* 253:6551-60 (1978)), the use of TAB® linkers (Pharmacia), and the like.

In a specific embodiment, relaxin analogs are prepared from relaxin-encoding nucleic acids that are altered to introduce aspartic acid codons at specific position(s) within at least a portion of the relaxin coding region. (See, e.g., U.S. Pat. No. 5,945,402, the disclosure of which is incorporated by reference herein.) The resulting analogs can be treated with dilute acid to release a desired analog, thereby rendering the protein more readily isolated and purified.

Manipulations of the relaxin polypeptide sequence can also be made at the polypeptide level. Included within the scope of the invention are relaxin analogs that are differentially modified during or after synthesis (e.g., in vivo or by in vitro translation). Such modifications include amino acid substitution (either conservative or non-conservative), glycosylation, acetylation, phosphorylation, amidation, derivatization by known protecting/blocking groups, proteolytic cleavage, linkage to an antibody molecule, a protein or other cellular ligand, and the like. Any of numerous chemical modifications can be carried out by known techniques, including, but not limited to, specific chemical cleavage (e.g., by cyanogen bromide), enzymatic cleavage (e.g., by trypsin, chymotrypsin, papain, V8 protease, and the like); modification by, for example, $NaBH_4$, acetylation, formylation, oxidation and reduction, metabolic synthesis in the presence of tunicamycin, and the like.

Relaxin analogs can be purified from natural sources by standard methods such as those described herein (e.g., immunoaffinity purification). Relaxin analogs can also be isolated and purified by standard methods including chromatography (e.g., ion exchange, affinity, sizing column chromatography, high pressure liquid chromatography), centrifugation, differential solubility, or by any other standard technique for the purification of polypeptides. Relaxin analogs can be synthesized by standard chemical methods known in the art (see, e.g., Hunkapiller et al., *Nature* 310:105-11 (1984); Stewart and Young, *Solid Phase Peptide Synthesis,* $2^{nd}$ Ed., Pierce Chemical Co., Rockford, Ill., (1984)). Furthermore, if desired, nonclassical amino acids or chemical amino acid analogs can be introduced as a substitution or addition into the relaxin polypeptide sequence. Non-classical amino acids include, but are not limited to, the D-isomers of the common amino acids, $\alpha$-amino isobutyric acid, 4-aminobutyric acid, 2-amino butyric acid, $\epsilon$-amino hexanoic acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, $\beta$-alanine, selenocysteine, fluoro-amino acids, designer amino acids such as $\beta$-methyl amino acids, C $\alpha$-methyl amino acids, N $\alpha$-methyl amino acids, and amino acid analogs in general. Furthermore, the amino acid can be D (dextrorotary) or L (levorotary).

In another embodiment, the relaxin analog is a chimeric, or fusion, protein comprising a relaxin polypeptide (typically consisting of at least a domain or motif of the relaxin polypeptide, or at least 10 contiguous amino acids of the relaxin polypeptide) joined at its amino- or carboxy-terminus via a peptide bond to an amino acid sequence of a different protein. In one embodiment, such a chimeric protein is produced by recombinant expression of a nucleic acid encoding the chimeric polypeptide. The chimeric product can be made by ligating the appropriate nucleic acid sequences, encoding the desired amino acid sequences, to each other in the proper reading frame and expressing the chimeric product by methods commonly known in the art. Alternatively, the chimeric product can be made by protein synthetic techniques (e.g., by use of an automated peptide synthesizer).

In a specific embodiment, the fusion protein is a relaxin analog-ubiquitin fusion protein. For example, U.S. Pat. No. 5,108,919 (the disclosure of which is incorporated herein by reference), discloses methods for preparing a fusion protein of a relaxin chain and ubiquitin.

Nucleic Acids:

The invention further provides nucleic acids for use as an antagonist, or for expressing an antagonist, according to the present invention. Such nucleic acids include those encoding a soluble relaxin receptor or a relaxin analog for synthesis of soluble relaxin receptor or relaxin analog, respectively. Antisense nucleic acids are provided for inhibition of relaxin or relaxin receptor expression. Nucleic acids encoding a relaxin polypeptide or a relaxin receptor polypeptide are also provided for the preparation of antibodies (see supra).

In one aspect, the invention provides nucleic acid sequences encoding a relaxin receptor or relaxin analog for expression in vivo. The relaxin receptor or relaxin analog, or antisense nucleic acids, can be expressed in vivo for gene therapy. Relaxin receptor, relaxin analog or antisense nucleic acids can also be expressed in vivo or in vitro for the production of recombinant soluble relaxin receptor, relaxin analog or antisense nucleic acids for exogenous administration to a subject.

The nucleic acids can be vertebrate nucleic acid, including, for example, human, mouse, rat, pig, cow, dog, or monkey relaxin receptor, relaxin, or a relaxin analog derived from a vertebrate relaxin. The nucleic acids can comprise genomic DNA, cDNA, or the coding region of the relaxin receptor, relaxin or a relaxin analog. The nucleic acids can further include mRNAs corresponding to the relaxin receptor locus or the relaxin locus. The nucleic acids also include nucleotide sequence variants, such as those encoding other possible codon choices for the same amino acid or conservative amino acid substitutions thereof, such as naturally occurring allelic variants. Due to the degeneracy of nucleotide coding sequences, other nucleic acid sequences which encode substantially the same amino acid sequence as a relaxin receptor or relaxin coding sequence, can be used in the practice of the present invention. These nucleic acid sequences include, but are not limited to, nucleotide sequences comprising all or portions of a relaxin gene which is altered by the substitution of different codons that encode the same or a functionally equivalent amino acid residue (e.g., a conservative substitution) within the sequence, thus producing a silent change.

The invention further provides nucleic acid fragments of at least 6 contiguous nucleotides (e.g., a hybridizable portion); in other embodiments, the nucleic acids comprise at least 8 contiguous nucleotides, at least contiguous 25 nucleotides, at least contiguous 50 nucleotides, at least 100 nucleotides, 150 nucleotides or more of a relaxin sequence. In another embodiment, the nucleic acids are smaller than 100 or 150 nucleotides in length. The nucleic acids can be single or double-stranded. As is readily apparent, as used herein, a nucleic acid encoding a fragment of a relaxin or relaxin receptor polypeptide is construed as referring to a nucleic acid encoding only the recited fragment or portion of the relaxin polypeptide and not the other contiguous portions of the relaxin receptor or relaxin polypeptide as a contiguous sequence. Fragments of the nucleic acids encoding one or more domains of relaxin or relaxin receptor are also provided.

Relaxin receptor, relaxin analog or antisense nucleic acids can be inserted into an appropriate vector (e.g., an expression vector which contains the necessary elements for the transcription or transcription and translation of the inserted polypeptide-coding sequence) in either the sense or antisense orientations, as desired. The necessary transcriptional and translational signals can also be supplied by the native relaxin or relaxin receptor gene and/or its flanking regions. A variety of host-vector systems can be utilized to express the polypeptide-coding sequence. These include but are not limited to, mammalian cell systems infected with virus (e.g., vaccinia virus, adenovirus, adeno-associated virus, and the like), insect cell systems infected with virus (e.g., baculovirus), microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any of a number of suitable transcription and translation elements can be used. In specific embodiments, the nucleic acids are expressed, or a nucleic acid sequence encoding a functionally active portion of a relaxin receptor or relaxin analog is expressed in mammalian cells, yeast or bacteria. In yet another embodiment, a fragment of a relaxin receptor or relaxin analog comprising a domain of the respective polypeptide is expressed.

Any of the methods known in the art for the insertion of nucleic acids into a vector can be used to construct expression vectors containing a chimeric gene having the appropriate transcriptional, translational control signals and/or polypeptide coding sequences. These methods include in vitro recombinant DNA and synthetic techniques and in vivo recombinants (genetic recombination). Expression of nucleic acids encoding a relaxin receptor or relaxin analog can be regulated by a second nucleic acid sequence so that the nucleic acid or polypeptide is expressed in a host transformed with the recombinant DNA molecule. For example, expression of a nucleic acid of a relaxin receptor or relaxin analog can be controlled by any promoter/enhancer element known in the art. Promoters which can be used to control expression include, but are not limited to, the SV40 early promoter region (see, e.g., Benoist and Chambon, *Nature* 290:304-10 (1981)), the promoter contained in the 3' long terminal repeat of Rous sarcoma virus (see, e.g., Yamamoto et al., *Cell* 22:787-97 (1980)), the herpes thymidine kinase promoter (see, e.g., Wagner et al., *Proc. Natl. Acad. Sci. USA* 78:1441-45 (1981)), the regulatory sequences of the metallothionen gene (see, e.g., Brinster et al., *Nature* 296:39-42 (1982)), prokaryotic expression vectors such as the β-lactamase promoter (see, e.g., Villa-Komaroff et al., *Proc. Natl. Acad. Sci. USA* 75:3727-31 (1978)) or the tac promoter (see, e.g., deBoer et al., *Proc. Natl. Acad. Sci. USA* 80:21-25 (1983)), plant expression vectors including the cauliflower mosaic virus 35S RNA promoter (see, e.g., Gardner et al., *Nucl. Acids Res.* 9:2871-88 (1981)), and the promoter of the photosynthetic enzyme ribulose biphosphate carboxylase (see, e.g., Herrera-Estrella et al., *Nature* 310:115-20 (1984)), promoter elements from yeast or other fungi such as the Gal7 and Gal4 promoters, the ADH (alcohol dehydrogenase) promoter, the PGK (phosphoglycerol kinase) promoter, the alkaline phosphatase promoter, and the like.

The following animal transcriptional control regions, which exhibit tissue specificity, have been utilized in transgenic animals: the elastase I gene control region which is active in pancreatic acinar cells (see, e.g., Swift et al., *Cell* 38:639-46 (1984); Ornitz et al., *Cold Spring Harbor Symp. Quant. Biol.* 50:399-409 (1986); MacDonald, *Hepatology* 7(1 Suppl.):42S-51S (1987)); the insulin gene control region which is active in pancreatic beta cells (see, e.g., Hanahan, *Nature* 315:115-22 (1985)), the immunoglobulin gene control region which is active in lymphoid cells (see, e.g., Grosschedl et al., *Cell* 38:647-58 (1984); Adams et al., *Nature* 318:533-38 (1985); Alexander et al., *Mol. Cell. Biol.* 7:1436-44 (1987)), the mouse mammary tumor virus control region which is active in testicular, breast, lymphoid and mast cells (see, e.g., Leder et al., *Cell* 45:485-95 (1986)), the albumin gene control region which is active in liver (see, e.g., Pinkert et al., *Genes Dev.* 1:268-76 (1987)), the alpha-fetoprotein gene control region which is active in liver (see, e.g., Krumlauf et al., *Mol. Cell. Biol.* 5:1639-48 (1985); Hammer et al., *Science* 235:53-58 (1987)); the alpha 1-antitrypsin gene control region which is active in the liver (see, e.g., Kelsey et al., *Genes and Devel.* 1:161-71 (1987)); the beta-globin gene control region which is active in myeloid cells (see, e.g., Magram et al., *Nature* 315:338-40 (1985); Kollias et al., *Cell* 46:89-94 (1986)); the myelin basic protein gene control region which is active in oligodendrocyte cells in the brain (see, e.g., Readhead et al., *Cell* 48:703-12 (1987)); the myosin light chain-2 gene control region which is active in skeletal muscle (see, e.g., Shani, *Nature* 314:283-86 (1985)); and the gonadotropic releasing hormone gene control region which is active in the hypothalamus (see, e.g., Mason et al., *Science* 234:1372-78 (1986)). In a preferred embodiment, the tissue-specific promoter is the prostate specific antigen promoter. (See, e.g., U.S. Pat. No. 6,100,444, the disclosure of which is incorporated by reference herein.)

In another embodiment, a vector is used that comprises a promoter operably linked to a nucleic acid, one or more origins of replication, and, optionally, one or more selectable markers (e.g., an antibiotic or drug resistance marker). For example, an expression construct can be made by subcloning a relaxin receptor or relaxin analog nucleic acid into a restriction site of the pRSECT expression vector. Such a construct allows for the expression of the relaxin analog or relaxin receptor polypeptide under the control of the T7 promoter with a histidine amino terminal flag sequence for affinity purification of the expressed polypeptide. In another specific embodiment, a vector is used that comprises the prostate specific antigen promoter operably linked to a relaxin analog nucleic acid, one or more origins of replication, and, optionally, one or more selectable markers (e.g., a drug resistance marker).

Expression vectors containing such nucleic acids can be identified by general approaches well known to the skilled artisan, including: (a) nucleic acid hybridization or polymerase chain reaction, (b) the presence or absence of "marker" gene function, (c) expression of inserted sequences, or polymerase chain reaction (PCR). In the first approach, the presence of a nucleic acid inserted in an expression vector can be detected by nucleic acid hybridization or polymerase chain reaction using probes comprising sequences that are homologous to an inserted nucleic acid. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, and the like) caused by the insertion of a vector containing the relaxin receptor, relaxin or relaxin analog nucleic acids.

For example, if the nucleic acid is inserted within the marker gene sequence of the vector, recombinants containing the nucleic acid can be identified by the absence of the marker gene function.

In the third approach, recombinant expression vectors can be identified by assaying the polypeptide expressed by the recombinant. Such assays can be based, for example, on the physical or functional properties of the polypeptide in in vitro assay systems (e.g., binding with anti-relaxin antibody, binding relaxin or a relaxin analog, binding to relaxin receptor, and the like). Once a particular recombinant vector is identified and isolated, several methods that are known in the art can be used to propagate it. Once a suitable host system and growth conditions are established, recombinant expression vectors can be propagated and prepared in quantity. As previously explained, the expression vectors which can be used include, but are not limited to the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few. In the fourth approach, PCR is used to detect the nucleic acid in the vector (see supra).

In addition, a host cell strain can be chosen that modulates the expression of the inserted sequences, or modifies or processes the gene product in the specific fashion desired. Expression from certain promoters can be elevated in the presence of certain inducers; thus, expression of the polypeptide can be controlled. Furthermore, different host cells having characteristic and specific mechanisms for the translational and post-translational processing, and modification (e.g., glycosylation, phosphorylation) of polypeptides can be used. Appropriate cell lines or host systems can be chosen to ensure the desired modification and processing of the foreign protein expressed. For example, expression in a bacterial system can be used to produce an unprocessed core protein product. Expression in mammalian cells can be used to ensure "native" processing of mammalian receptor polypeptide. Furthermore, different vector/host expression systems can affect processing reactions to different extents.

Functional Assays for Relaxin and Relaxin Receptor Agonists and Antagonists

The activity of relaxin agonists and antagonists, and of relaxin receptor agonists and antagonists, can be determined by standard assays for relaxin and/or relaxin receptor activity. In one aspect of the invention, the activity of a relaxin agonist is assayed. For example, the ability of a relaxin agonist to decrease apoptosis, or to stimulate maturation of tissue, is assayed.

In another aspect of the invention, the ability of a relaxin antagonist to inhibit relaxin functional activity by binding to relaxin is assayed. Similarly, the ability of a relaxin antagonist to inhibit relaxin function, or relaxin receptor function, can be assayed by, for example, adding a relaxin antagonist to a relaxin receptor assay and determining the inhibition, as compared with a control without the relaxin antagonist. Suitable measurements of relaxin antagonist activity include measuring percent inhibition, $IC_{50}$, and the like.

Suitable assays for measuring relaxin or relaxin receptor agonist or antagonist activity, include, for example, those described in the following references (which are incorporated by reference herein): MacLennan et al., Ripening of the Human Cervix and Induction of Labor with Intracervical Purified Porcine Relaxin, *Obstetrics & Gynecology* 68:598-601 (1986); Poisner et al., Relaxin Stimulates the Synthesis and Release of Prorenin From Human Decidual Cells: Evidence For Autocrine/Paracrine Regulation, *J. Clinical Endocrinology and Metabolism* 70:1765-67 (1990); O'Day-Bowman et al., Hormonal Control of the Cervix in Pregnant Gilts. III. Relaxin's Influence on Cervical Biochemical Properties in Ovariectomized Hormone-Treated Pregnant Gilts, *Endocrinology* 129:1967-76 (1991); Saugstad, Persistent Pelvic Pain and Pelvis Joint Instability, *Eur. J. Obstetrics & Gynecology and Reproductive Biology* 41:197-201 (1991).

Other assays include those disclosed by Bullesbach et al., The Receptor-Binding Sites of Human Relaxin II, *J. Biol. Chem.* 267:22957-60 (1992); Hall et al., Influence of Ovarian Steroids on Relaxin-Induced Uterine Growth in Ovariectomized Gilts, *Endocrinology* 130:3159-66 (1992); Kibblewhite et al., The Effect of Relaxin on Tissue Expansion, *Arch. Otolaryngol. Head Neck Surg.* 118:153-56 (1992); Lee et al., Monoclonal Antibodies Specific for Rat Relaxin. VI. Passive Immunization with Monoclonal Antibodies Throughout the Second Half of Pregnancy Disrupts Histological Changes Associated with Cervical Softening at Parturition in Rats, *Endocrinology* 130:2386-91 (1992); Bell et al., A Randomized, Double-Blind Placebo-Controlled Trial of the Safety of Vaginal Recombinant Human Relaxin for Cervical Ripening, *Obstetrics & Gynecology* 82:328-33 (1993); Bryant-Greenwood et al., Sequential Appearance of Relaxin, Prolactin and IGFBP-1 During Growth and Differentiation of the Human Endometrium, *Molecular and Cellular Endocrinology* 95:23-29 (1993); Chen et al., The Pharmacokinetics of Recombinant Human Relaxin in Nonpregnant Women After Intravenous, Intravaginal, and Intracervical Administration, *Pharmaceutical Research* 10:834-38 (1993); Huang et al., Stimulation of Collagen Secretion by Relaxin and Effect of Oestrogen on Relaxin Binding in Uterine Cervical Cells of Pigs, *Journal of Reproduction and Fertility* 98:153-58 (1993);

Additional assays are disclosed in Saxena et al., Is the Relaxin System a Target for Drug Development? Cardiac Effects of Relaxin, *TiPS* 14:231 (June 1993, letter); Winn et al., Hormonal Control of the Cervix in Pregnant Gilts. IV. Relaxin Promotes Changes in the Histological Characteristics of the Cervix that are Associated with Cervical Softening During Late Pregnancy in Gilts, *Endocrinology* 133:121-28 (1993); Colon et al., Relaxin Secretion into Human Semen Independent of Gonadotropin Stimulation, *Biology of Reproduction* 50:187-92 (1994); Golub et al., Effect of Short-Term Infusion of Recombinant Human Relaxin on Blood Pressure in the Late-Pregnant Rhesus Macaque (Macaca Mulatta), *Obstetrics & Gynecology* 83:85-88 (1994); Jauniaux et al., The Role of Relaxin in the Development of the Uteroplacental Circulation in Early Pregnancy, *Obstetrics & Gynecology* 84:338-342 (1994); Johnson et al., The Regulation of Plasma Relaxin Levels During Human Pregnancy, *J. Endocrinology* 142:261-65 (1994); Lane et al., Decidualization of Human Endometrial Stromal Cells in Vitro: Effects of Progestin and Relaxin on the Ultrastructure and Production of Decidual Secretory Proteins, *Human Reproduction* 9:259-66 (1994); Lanzafame et al., Pharmacological Stimulation of Sperm Motility, *Human Reproduction* 9:192-99 (1994); Petersen et al., Normal Serum Relaxin in Women with Disabling Pelvic Pain During Pregnancy, *Gynecol. Obstet. Invest.* 38:21-23 (1994); Tashima et al., Human Relaxins in Normal, Benign and Neoplastic Breast Tissue, *J. Mol. Endocrinology* 12:351-64 (1994); Winn et al. Individual and Combined Effects of Relaxin, Estrogen, and Progesterone in Ovariectomized Gilts. I. Effects on the Growth, Softening, and Histological Properties of the Cervix, *Endocrinology* 135:1241-49 (1994); Winn et al., Individual and Combined Effects of Relaxin, Estrogen, and Progesterone on Ovariectomized Gilts. II. Effects on Mammary Development, *Endocrinology* 135:1250-55 (1994); Bryant-Greenwood et al., Human Relaxins: Chemistry and Biology, *Endocrine Reviews* 15:5-26 (1994); Johnson et al., Relationship Between Ovarian Steroids, Gonadotrophins and Relaxin During the Menstrual Cycle, *Acta Endocrinilogica* 129:121-25 (1993).

In yet another aspect of the invention, the activity of an agonist or antagonist is determined by measuring the ability of the agonist or antagonist to compete with wild-type relaxin polypeptide, or relaxin receptor polypeptide, for binding to anti-relaxin antibody. Various immunoassays known in the art can be used. Such assays include, but are not limited to, competitive and non-competitive assay systems using techniques such as radioimmunoassays, ELISA (enzyme linked immunosorbent assay) "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays or hemagglutination assays), complement fixation assays, immunofluorescence assays, protein A assays, immunoelectrophoresis assays, and the like. Antibody binding can be detected by measuring the amount of label on the primary antibody that is bound, or prevented from binding to, a substrate. Alternatively, primary antibody binding is detected by measuring binding of a secondary antibody or reagent to the primary antibody. The secondary antibody can also be directly labeled. Many means are known in the art for detecting binding in an immunoassay and are considered within the scope of the present invention.

The functional activity of an agonist or antagonist can also be determined in an in vivo system. For example, the ability of relaxin agonists or antagonists to bind, or to compete for binding to, a relaxin receptor, or to modulate apoptosis in a cell population and/or tissues can be measured. The assays described above can be used to determine the activity resulting from expression of relaxin agonist or antagonists in vertebrate cells. Alternatively, relaxin agonist or antagonist can be expressed in a heterologous system and the activity of the relaxin agonist or antagonist can be assayed as a modulator of a physiological change in that system. For example, the ability of a relaxin agonist or antagonist to modulate apoptosis can be tested in vertebrate cells (e.g., transfected mammalian cells).

Administration of Relaxin Agonists and Antagonists

The invention provides methods for the administration to a subject of an effective amount of a relaxin agonist or antagonist (also referred to collectively as an "active agent"). Typically, the active agent is substantially purified prior to formulation. The subject can be a human or non-human animal, a vertebrate, and is typically an animal, including but not limited to, cows, pigs, horses, chickens, cats, dogs, and the like. More typically, the subject is a mammal, and in a particular embodiment, human.

Various delivery systems are known and can be used to administer a active agent, such as, for example, by infusion, injection (e.g., intradermal, intramuscular or intraperitoneal), oral delivery, nasal delivery, intrapulmonary delivery, rectal delivery, transdermal delivery, interstitial delivery or subcutaneous delivery. In a specific embodiment, it can be desirable to administer the active agent locally to the area in need of treatment; this administration can be achieved by, for example, and not by way of limitation, local infusion, topical application, by injection (e.g., intratesticular or intraprostatic), by means of a catheter, or by means of an implant, the implant being for example, a porous, non-porous, gelatinous or polymeric material, including membranes such as silastic membranes or fibers. In one embodiment, administration can be by direct injection at the target site.

Pharmaceutical compositions containing the active agent can be formulated according to the desired delivery system. Such pharmaceutical compositions typically comprise a therapeutically effective amount of active agent and a pharmaceutically acceptable carrier. The term "pharmaceutically acceptable" means approved by a regulatory agency of the Federal or a state government or listed in the U.S. Pharmacopeia or other generally recognized pharmacopeia for use in vertebrates, typically animals, and more typically in humans. The term "carrier" refers to a diluent, adjuvant, excipient, stabilizer, preservative, viscogen, or vehicle with which the active agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, ethanol, and the like. The composition, if desired, can also contain minor amounts of wetting or emulsifying agents, or pH buffering agents.

Suitable preservatives include, for example, sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, potassium benzoate, potassium metabisulfite, potassium sorbate, sodium bisulfite, sulfur dioxide, organic mercurial salts, phenol and ascorbic acid. Suitable viscogens include, for example, carboxymethylcellulose, sorbitol, dextrose, and polyethylene glycols. Other examples of suitable pharmaceutical carriers are described in, for example, *Remington's Pharmaceutical Sciences* (Gennaro (ed.), Mack Publishing Co., Easton, Pa. (1990)). The active agents can also be formulated as neutral or salt forms.

Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

In one embodiment, the active agent is formulated in accordance with routine procedures as a pharmaceutical composition adapted for intravenous administration to human beings. For intravenous delivery, water is a typical carrier. Saline, aqueous dextrose and glycerol solutions can also be employed as liquid carriers, particularly for injectable solutions. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water-free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Orally deliverable compositions can take the form of solutions, suspensions, emulsions, tablets, pills, capsules, powders, sustained-release formulations, and the like. Oral formulations can include standard carriers such as pharmaceutical grades of mannitol, lactose, starch, magnesium stearate, sodium saccharine, cellulose, magnesium carbonate, and the like.

For rectal administration, the compositions are formulated according to standard pharmaceutical procedures. Typically, the composition is formed as a meltable composition, such as a suppository. Suppositories can contain adjuvants which provide the desired consistency to the composition. They can also contain water-soluble carriers, such as polyethylene glycol, polypropylene glycol, glycerogelatine, methylcellulose or carboxymethylcellulose. Wetting agents, such as fatty acids, fatty acid glycerides, polyoxyethylene sorbitan fatty acid esters, polyoxyethylene sorbitol fatty acid esters, polyoxyethylene fatty acid esters, as well as higher alcohol esters of polyoxyethylene and esters of lower alkylsulfonic acids. The suppositories can also contain suitable emulsifying and dispersing components as well as components for adjusting the viscosity and coloring substances.

Nasal administration is typically performed using a solution as a nasal spray and can be dispensed by a variety of methods known to those skilled in the art. Systems for intranasally dispensing liquids as a spray are well known (see, e.g., U.S. Pat. No. 4,511,069, which is incorporated by reference herein). Preferred nasal spray solutions comprise the active agent in a liquid carrier that optionally includes a nonionic surfactant for enhancing absorption of the drug and one or more buffers or other additives to minimize nasal irritation. In some embodiments, the nasal spray solution further comprises a propellant. The pH of the nasal spray solution is typically between about pH 6.8 and 7.2.

For intranasal administration, ingredients which improve the absorption of nasally administered active agent and reduce nasal irritation, especially when used in a chronically administered treatment protocol, are desirable. In this context, the utilization of surfactants to enhance absorption of the active agent is preferred. (See, e.g., Hirai et al., *Int. J. Pharmaceutics* 1:173-84 (1981); Great Britain Patent Specification 1 527 605, each of which is incorporated by reference herein.) Nasal administration of drugs enhanced by surfactants, however, can cause nasal irritation, including stinging, congestion and rhinorrhea. Thus, compositions which enhance absorption through the nasal mucosa with reduced irritation are desirable, such as, for example, nonionic surfactants such as nonoxynol-9, laureth-9, poloxamer-124, octoxynol-9 and lauramide DEA. Nonoxynol-9 (N-9) is an ethoxylated alkyl phenol, the polyethyleneoxy condensate of nonylphenol with 9 moles of ethylene oxide. This surfactant has been used in detergent products and is sold under trade names such as SURFONIC® N-95 (Jefferson), NEUTRONYX® 600 (Onyx) and IGEPAL® (CO-630 (GAF). N-9 is considered to be a hard detergent, and has been used as a spermatocide. (*See The Merck Index*, 10$^{th}$ Ed., Entry 6518). To minimize irritation attributed to employment of surfactants, one or more anti-irritant additives are included in the emulsion. In one example, polysorbate-80 has been shown to reduce the irritation caused by intranasally administered drugs where delivery was enhanced by use of a nonionic surfactant (see, e.g., U.S. Pat. No. 5,902,789, which is incorporated by reference herein).

Intrapulmonary dosage forms containing the active agent can be administered to the respiratory tract intranasally or by breathing a spray or aerosol containing the active agent. The active agent is typically delivered directly into the lungs in a small particle aerosol, which is specifically targeted to the smallest air passages and alveoli.

Intrapulmonary dosage forms are typically formed as particulate dispersed forms. This can be accomplished by preparing an aqueous aerosol of solid particles which contain the composition. Typically, an aqueous aerosol is made by formulating an aqueous solution or suspension of the composition together with conventional pharmaceutically acceptable carriers and stabilizers. The carriers and stabilizers typically include nonionic surfactants (e.g., Tweens, Pluronics or polyethylene glycol), innocuous proteins such as serum albumin, sorbitan esters, oleic acid, amino acids such as glycine, buffers, salts, sugars or sugar alcohols. The formulations can also include mucolytic agents, such as those described in U.S. Pat. No. 4,132,803 (which is incorporated by reference herein), as well as broncho-dilating agents. The formulations are preferably sterile. Aerosols are generally prepared from isotonic solutions. The particles optionally include normal lung surfactant proteins.

The aerosol of particles can be formed in aqueous or nonaqueous (e.g., fluorocarbon propellant) suspensions. The aerosols are preferably free of lung irritants (i.e., substances that cause acute bronchoconstriction, coughing, pulmonary edema or tissue destruction). Nonirritating, absorption enhancing agents are also suitable for use herein.

Sonic nebulizers can be used to prepare aerosols. Sonic nebulizers minimize exposure of the composition to shear, which can result in degradation. A suitable device is the Bird Micronebulizer. Other suitable atomizing or nebulizing systems or intratracheal delivery systems include, for example, those disclosed in U.S. Pat. No. 3,915,165; European Patent No. 0 166 476; the jet nebulizers described by Newman et al. (*Thorax* 40:671-76 (1985)); metered dose inhalers (see, e.g., Berenberg, *J. Asthma-USA* 22:87-92 (1985)); the endotracheal catheter assembly of Braunner (U.S. Pat. No. 5,803,078), or other devices (see, e.g., Sears et al., *N.Z. Med. J.* 96:74311 (1983); O'Reilly et al., *Br. Med. J.* 286:6377 (1983); or Stander et al., *Respiration* 44:237-40 (1982)), so long as they are compatible with the composition to be administered and are capable of delivering particles of the desired size. (The disclosures of these references are incorporated by reference herein.)

The particulate aerosol suspensions are typically fine dry powders containing the active agent. Particulate aerosol suspension are prepared by any number of conventional procedures. The simplest method of preparing such suspensions is to micronize the active agent (e.g., as crystals or lyophilization cakes), and suspend the particles in dry fluorocarbon propellants. In these formulations the active agent is preferably suspended in the fluorocarbon. In an alternate embodiment, the active agent is stored in a compartment separate from the propellant. Discharge of the propellant withdraws a predetermined dose from the storage compartment. The devices used to deliver active agents in this manner are known as metered dose inhalers (MDIs) (see, e.g., Byron, *Drug Development and Industrial Pharmacy* 12:993 (1986), which is incorporated by reference herein).

The size of the aerosols or particles generally will range about from 0.5 to about 5 µm, typically about 2 µm to 5 µm, preferably about 2 to about 4 µm or about 4 to about 5 µm. In some aspects, smaller particles are less acceptable because they tend not to be deposited, but instead are exhaled. Similarly, in other aspects, larger particles are not preferred because they are less likely to be deposited in the alveoli, being removed by impaction within the nasopharyngeal or oral cavities (see, e.g., Byron, *J. Pharm. Sci.* 75:433 (1986)). The aerosol or particulate compositions can be heterogeneous in size distribution, although heterogeneity can be reduced by known methods (e.g., the screening unit described in EP 0 135 390). Heterogeneity is typically not disadvantageous unless the proportion of particles having an average mean diameter in excess of about 4 µm is so large as to impair the delivery of a therapeutic dose by pulmonary inhalation. Suspensions containing greater than about 15% of particles within the 0.5-5 µm range can be used, but generally the proportion of particles having an average mean diameter larger than 5 µm is typically less than about 25%, and preferably not greater than 10%, of the total number of particles. The diameters recited refer to the particle diameters as introduced into the respiratory tract.

The amount of the active agent which will be effective in the treatment of a particular subject will depend on the specific abnormality being treated, and can be determined by standard clinical techniques. In addition, in vitro assays can optionally be employed to help identify optimal dosage ranges. The precise dose of the active agent to be employed in the formulation will also depend on the route of administration, and the seriousness of the condition, and should be decided according to the judgment of the practitioner and each subject's circumstances. Suitable dosage ranges for administration are generally about 0.001 mg/kg to about 100 mg/kg of active agent per kilogram body weight. Effective doses can also be extrapolated from dose response curves derived from in vitro or animal model test systems. Suppositories generally contain active ingredient in the range of 0.5% to 10% by weight; oral formulations typically contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In yet another embodiment, the active agent can be delivered in a controlled release system. In one embodiment, a pump can be used (see, e.g., Langer, supra; Sefton, *Crit. Ref Biomed. Eng.* 14:201-40 (1987); Buchwald et al., *Surgery* 88:507-16 (1980); Saudek et al., *N. Engl. J. Med.* 321:574-79 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228:190-92 (1985); During et al., *Ann. Neurol.* 25:351-56 (1989); Howard et al., *J. Neurosurg.* 71:105-12 (1989)) (the disclosures of which are incorporated by reference herein).

In yet another embodiment, a controlled release system can be placed in proximity of the therapeutic target, thus requiring only a fraction of the systemic dose (see, e.g., Goodson, *Medical Applications of Controlled Release, supra*, Vol. 2, pp. 115-38 (1984)). Other controlled release systems are discussed in, for example, the review by Langer (*Science* 249:1527-33 (1990), which is incorporated by reference herein).

Administration of Nucleic Acids

The invention provides further methods for the administration of nucleic acids (e.g., nucleic acids encoding relaxin agonists or antagonists, such as relaxins, relaxin analogs, soluble relaxin receptor, relaxin binding agents, relaxin receptor binding agents, relaxin antisense nucleic acids and/or relaxin receptor antisense nucleic acids) to modulate apoptosis. Nucleic acids, both sense and antisense, can be used in the process of gene therapy. Gene therapy refers to the process of providing for the expression of nucleic acids of exogenous origin, including antisense nucleic acids or those encoding relaxin agonist or antagonist in a subject for the modulation of apoptosis (e.g. to treat a tissue abnormality) within the subject. In specific embodiments, nucleic acids encoding a relaxin or a relaxin analog are administered to decrease apoptosis in cells have a relaxin receptor. In other specific embodiments, nucleic acids encoding a relaxin binding agent (e.g., a relaxin a soluble relaxin receptor) or a relaxin receptor binding agent (e.g., a relaxin analog) is administered to increase apoptosis in a cell population expressing a relaxin receptor. Any of the methods for gene therapy available in the art can be used according to the present invention. Exemplary methods are described below.

For general reviews of the methods of gene therapy, see Steinberg and Raso (*J. Pharm. Pharm. Sci.* 1:48-59 (1998)); Pantuck et al. (*World J. Urol.* 18:143-47 (2000)); Prince (*Pathology* 30:335-47 (1998)); Ledley (*Curr. Opin. Biotechnol.* 5:626-36 (1994)); Goldspiel et al. (*Clin. Pharm.* 12:488-505 (1993)); Wu and Wu (*Biotherapy* 3:87-95 (1991)); Tolstoshev (*Ann. Rev. Pharmacol. Toxicol.* 32:573-96 (1993)); Mulligan (*Science* 260:926-32 (1993)); Morgan and Anderson (*Ann. Rev. Biochem.* 62:191-217 (1993)); and May (*TIBTECH* 11:155-215 (1993)).

Methods commonly known in the art of recombinant DNA technology that can be used include those described in Ausubel et al. (1996, supra) and Kriegler (*Gene Transfer and Expression, A Laboratory Manual*, Stockton Press, NY (1990)). In one embodiment, the nucleic acid comprises a sense nucleic acid (e.g., encoding a relaxin analog, soluble relaxin receptor, and the like) that is part of a vector that expresses the nucleic acid in a suitable host. In particular, such a nucleic acid has a promoter operably linked to the coding region (e.g., relaxin or relaxin receptor) in a sense orientation, the promoter being inducible or constitutive, and, optionally, tissue-specific. In another embodiment, the nucleic acid comprises an antisense nucleic acid (e.g., a relaxin antisense nucleic acid or relaxin receptor antisense nucleic acid) that is part of a vector that expresses the nucleic acid in a suitable host. In particular, such a nucleic acid has a promoter operably linked to the coding region (e.g., relaxin or relaxin receptor) in an antisense orientation, the promoter being inducible or constitutive, and, optionally, tissue-specific.

In another particular embodiment, a nucleic acid (e.g., a sense nucleic acid encoding a relaxin analog, soluble relaxin receptor, and the like, or an antisense nucleic acid encoding a relaxin antisense nucleic acid, a relaxin receptor antisense nucleic acid, and the like) used in which the nucleic acid and any other desired sequences are flanked by regions that promote homologous recombination at a desired site in the genome, thus providing for intrachromosomal expression of the nucleic acid (see, e.g., Koller and Smithies, *Proc. Natl. Acad. Sci. USA* 86:8932-35 (1989); Zijlstra et al., *Nature* 342:435-38 (1989); U.S. Pat. Nos. 5,631,153; 5,627,059; 5,487,992; and 5,464,764; the disclosures of which are incorporated by reference herein).

For any of these embodiments, delivery of the nucleic acid into a subject can be either direct, in which case the subject is directly exposed to the nucleic acid or nucleic acid-carrying vector, or indirectly, in which case cells are first transformed with the nucleic acid in vitro, and then transplanted into the subject. These two approaches are known, respectively, as in vivo or ex vivo gene therapy. In a specific embodiment, the nucleic acids are directly administered in vivo, where they are expressed to produce the encoded product. This can be accomplished by any of numerous methods known in the art (e.g., by constructing it as part of an appropriate nucleic acid expression vector and administering it so that it becomes intracellular, for example, by infection using a defective or attenuated retroviral or other viral vector (infra), by direct injection of naked DNA (see, e.g., Asahara et al., *Semin. Interv. Cardiol.* 1:225-32 (1996); Prazeres et al., *Trends Biotechnol.* 17:169-74 (1999); the disclosures of which are incorporated by reference herein), electroporation (see, e.g., Muramatsu et al., *Int. J. Mol. Med.* 1:55-62 (1998), the disclosure of which is incorporated by reference herein), or by use of microparticle bombardment, such as a gene gun (BIOLISTIC™, Dupont); see, e.g., Biewenga et al., *J. Neurosci. Methods* 71:67-75 (1997), the disclosure of which is incorporated by reference herein). Nucleic acids can also be inserted into cells by coating naked nucleic acids with lipids or cell-surface receptors or transfection agents, encapsulation in liposomes, derivatized liposomes, microparticles, or microcapsules (see, e.g., De Smedt et al., *Pharm. Res.* 17:113-26 (2000); Maurer et al., *Mol. Membr. Biol.* 16:129-40 (1999); Tarahovsky and Ivanitsky, *Biochemistry* 63:607-18 (1998); Lasci, *Trends Biotechnol.* 16: 307-21 (1998); Gao and Huang, *Gene Ther.* 2:710-22 (1995); the disclosures of which are incorporated by reference herein). Nucleic acids can also be administered in linkage to a peptide which is known to enter the cell or by administering the nucleic acids in linkage to a ligand subject to receptor-mediated endocytosis, which can be used to target cell types specifically expressing the receptors, and the like. (See, e.g., Liang et al., *Pharmazie* 54:559-66 (1999); Cristiano, *Front. Biosci.* 15:D1161-70 (1998); Guy et al., *Mol. Biotechnol.* 3:237-48 (1995); Wu and Wu, *J. Biol. Chem.* 262:4429-32 (1987); the disclosures of which are incorporated by reference herein). In another embodiment, a nucleic acid-ligand complex can be formed in which the ligand comprises a fusogenic viral peptide to disrupt endosomes, allowing the nucleic acid to avoid lysosomal degradation. (See, e.g., Phillips, *Biologicals* 23:13-16 (1995), the disclosure of which is incorporated by reference herein.)

In yet another embodiment, the antisense nucleic acid can be targeted in vivo for cell specific uptake and expression by targeting a specific receptor (see, e.g., Phillips, *Biologicals* 23:13-16 (1995); International Patent Publications WO 92/06180; WO 92/22635; WO 92/20316; WO 93/14188, and WO 93/20221; the disclosures of which are incorporated by reference herein).

In a specific embodiment, a viral vector is used that contains the nucleic acid (e.g., a sense nucleic acid encoding a relaxin analog, soluble relaxin receptor, and the like, or an antisense nucleic acid encoding a relaxin antisense nucleic acid, a relaxin receptor antisense nucleic acid, and the like). For example, a retroviral vector can be used (see, e.g., Palu et al., *Rev. Med. Virol.* 10:185-202 (2000); Buchschacher and Wong-Staal, *Blood* 15:2499-504 (2000); Miller et al., *Meth. Enzymol.* 217:581-99 (1993), the disclosures of which are incorporated by reference herein). These retroviral vectors are typically modified to delete retroviral sequences that are not necessary for packaging of the viral genome and integration into host cell DNA. The antisense nucleic acid to be used in gene therapy is cloned into the vector, which facilitates delivery of the antisense nucleic acid into the subject. Lentiviral vectors can also be used. (See, e.g., Buchschacher and Wong-Staal, supra; Naldini et al., *Science* 272:263-67 (1996), the disclosures of which are incorporated by reference herein). Other references illustrating the use of viral vectors in gene therapy are by Lundstrom (*J. Recept. Signal. Transduct. Res.* 19:673-86 (1999)); Clowes et al. (*J. Clin. Invest.* 93:644-51 (1994)); Kiem et al. (*Blood* 83:1467-73 (1994)); Salmons and Gunzberg (*Hum Gene Ther.* 4:129-41 (1993)); and Grossman and Wilson (*Curr. Opin. Genet Dev.* 3:110-14 (1993)) (the disclosures of which are incorporated by reference herein).

Adenoviruses can also be used in gene therapy. Adenoviruses are especially attractive vehicles for delivering genes to prostate, liver, the central nervous system, endothelial cells, and muscle. Adenoviruses have the advantage of being capable of infecting non-dividing cells. Kozarsky and Wilson (*Curr. Opin. Genet Dev.* 3:499-503 (1993), the disclosure of which is incorporated by reference herein) present a review of adenovirus-based gene therapy. Herman et al. (*Human Gene Therapy* 10:1239-49 (1999), the disclosure of which is incorporated by reference herein) describe the intraprostatic injection of a replication-deficient adenovirus containing the herpes simplex thymidine kinase gene into human prostate, followed by intravenous administration of the prodrug ganciclovir in a phase I clinical trial. Other instances of the use of adenoviruses in gene therapy can be found in Rosenfeld et al. (*Science* 252:431-34 (1991)); Rosenfeld et al. (*Cell* 68:143-55 (1992)); Mastrangeli et al. (*J. Clin. Invest.* 91:225-34 (1993)); and Thompson (*Oncol. Res.* 11:1-8 (1999)). Adeno-associated virus (AAV) can also be used in gene therapy (see, e.g., Rabinowitz and Samulski, *Curr. Opin. Biotechnol.* 9:475-85 (1988); Carter and Samulski, *Int. J. Mol. Med.* 6:17-27 (2000); Tal, *J. Biomed. Sci.* 7:279-91 (2000); Ali et al., *Gene Therapy* 1:367-84 (1994); U.S. Pat. Nos. 4,797,368 and 5,139,941; Walsh et al., *Proc. Soc. Exp. Biol. Med.* 204:289-300 (1993); Grimm et al., *Human Gene Therapy* 10:2445-50 (1999)) (the disclosures of which are incorporated by reference herein).

Another approach to gene therapy involves transferring a nucleic acid to cells in tissue culture by methods such as electroporation, lipofection, calcium phosphate mediated transfection, or viral infection. Typically, the method of transfer includes the transfer of a selectable marker to the cells. The cells are then placed under selection to isolate those cells that have taken up and are expressing the nucleic acid. The selected cells are then delivered to a subject.

In one embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid, cell fusion, chromosome-mediated gene transfer, microcell-mediated gene transfer, and the like. Numerous techniques are known in the art for the introduction of foreign genes into cells (see, e.g., Muramatsu et al., *Int. J. Mol. Med.* 1:55-62 (1998); Liang et al., *Pharmazie* 54:559-66 (1999); Loeffler and Behr, *Meth. Enzymol.* 217:599-618 (1993); Cotten et al., *Meth. Enzymol.* 217:618-44 (1993); Cline, *Pharmacol. Ther.* 29:69-92 (1985); the disclosures of which are incorporated by reference herein) and can be used in accordance with the present invention. The technique typically provides for the stable transfer of the nucleic acids to the cell, so that the nucleic acids are expressible by the cell and is heritable and expressible by its cell progeny.

The resulting recombinant cells can be delivered to a subject by various methods known in the art. Typically, cells are injected subcutaneously. In another embodiment, recombinant skin cells can be applied as a skin graft onto the subject. The amount of cells required for use depends on the desired effect, the subject's condition, and the like, and can be determined by one skilled in the art.

Cells into which a nucleic acid can be introduced for purposes of gene therapy encompass any desired, available cell type, and include but are not limited to cells or populations of cells of the male reproductive tract (e.g., prostate cells, cells of the testes, seminiferous cells, or epididymal cells), female reproductive tract (e.g., uterus, cervix, the interpubic ligament, connective tissues within the pelvic girdle, and the like), liver, kidney, spleen, thymus, brain, heart, intestine, skin, lung, and the like. Suitable cells further include epithelial cells, endothelial cells, keratinocytes, fibroblasts, muscle cells, and stem or progenitor cells. The cells used for gene therapy generally are autologous to the subject, but heterologous cells that can be typed for compatibility with the subject can be used.

In another aspect, nucleic acids (e.g., a sense nucleic acid encoding a relaxin analog, soluble relaxin receptor, and the like, or an antisense nucleic acid encoding a relaxin antisense nucleic acid, a relaxin receptor antisense nucleic acid, and the like) are administered directly to cells. The nucleic acids are at least six nucleotides and are typically oligonucleotides (ranging from 6 to about 50 nucleotides or more). In specific aspects, the oligonucleotide is at least 10 nucleotides, at least 15 nucleotides, at least 100 nucleotides, or can be at least 200 nucleotides. The oligonucleotides can be DNA or RNA or chimeric mixtures or derivatives or analogs thereof, and can be single-stranded or double-stranded. The oligonucleotide can be modified at the base moiety, sugar moiety, or phosphate backbone. The oligonucleotide can include other appending groups such as peptides, or agents facilitating transport across the cell membrane (see, e.g., Nielsen, *Pharmacol. Toxicol.* 86:3-7 (2000); Soomets et al., *Front. Biosci.* 1:D782-86 (1999); Galderisi et al., *J. Cell Physiol.* 181:251-57 (1999); Letsinger et al., *Proc. Natl. Acad. Sci. USA* 86:6553-56 (1989); Lemaitre et al., *Proc. Natl. Acad. Sci. USA* 84:648-52 (1987); International Patent Publication WO 88/09810), hybridization-triggered cleavage agents (see, e.g., Krol et al., *BioTechniques* 6:958-76 (1988)) or intercalating agents (see, e.g., Zon, *Pharm. Res.* 5:539-49 (1988)). (The disclosures of these references are incorporated herein.)

In one embodiment, antisense oligonucleotides are provided as single-stranded DNA. The oligonucleotides can be modified at any position on its structure with substituents generally known in the art. The oligonucleotides can comprise at least one modified base moiety, such as, for example, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, 2,6-diaminopurine, and the like. In another embodiment, the oligonucleotides comprise at least one modified sugar moiety, such as, for example, arabinose, 2-fluoroarabinose, xylulose, and hexose.

In yet another embodiment, the antisense oligonucleotides comprise at least one modified phosphate backbone, such as, for example, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (see Gautier et al., *Nucl. Acids Res.* 15:6625-41 (1987)). The oligonucleotide can be conjugated to another molecule (e.g., a peptide, hybridization triggered cross-linking agent, transport agent, hybridization-triggered cleavage agent, and the like).

In a specific embodiment, the antisense oligonucleotide comprises catalytic RNA, or a ribozyme (see, e.g., Welch et al., *Curr. Opin. Biotechnol.* 9:486-96 (1998); Norris et al., *Adv. Exp Med. Biol.* 465:293-301 (2000); International Patent Publication WO 90/11364; Sarver et al., *Science* 247: 1222-25 (1990)). In another embodiment, the oligonucleotide is a 2'-0-methylribonucleotide (Inoue et al., *Nucl. Acids Res.* 15:6131-48 (1987)), or a chimeric RNA-DNA analogue (Inoue et al., *FEBS Lett.* 215:327-30 (1987)).

In another specific embodiment, double-stranded RNA directs the sequence-specific degradation of mRNA by RNA interference. (See generally Hunter, *Curr. Biol.* 10:R137-40 (2000); Bosher and Labouesse, *Nat. Cell. Biol.* 2:e31-36 (2000); the disclosures of which are incorporated by reference herein.) Briefly, double-stranded nucleic acids are introduced into a cell to selectively inhibit gene expression by causing degradation of the mRNA. (See, e.g., Zamore et al., *Cell* 101:25-33 (2000), the disclosure of which is incorporated by reference herein.)

Nucleic acids according to the present invention can be synthesized by standard methods known in the art. Enzymatic methods for the synthesis of nucleic acids frequently employ Klenow, T7, T4, Taq or *Escherichia coli* DNA polymerases, as described in Sambrook et al. (supra). Enzymatic methods of RNA nucleic acids frequently employ SP6, T3 or T7 RNA polymerases, as described in Sambrook et al. (supra). Reverse transcriptase can also be used to synthesize DNA from RNA (Sambrook et al., supra). Nucleic acids are typically prepared enzymatically using a template nucleic acid which can either be synthesized chemically, or be obtained as mRNA, genomic DNA, cloned genomic DNA, cloned cDNA or other nucleic acid. Some enzymatic methods of DNA nucleic acid synthesis can require an additional primer which can be synthesized chemically. Finally linear nucleic acids can be prepared by polymerase chain reaction (PCR) techniques as described, for example, by Saiki et al. (*Science* 239:487 (1988)).

Chemical methods can also be used to synthesize nucleic acids (e.g., antisense oligonucleotides), such as by use of a commercially available automated DNA synthesizer). As examples, phosphorothioate nucleic acids can be synthesized by the method of Stein et al. (*Nucl. Acids Res.* 16:3209-21 (1988)), methylphosphonate nucleic acids can be prepared by use of controlled pore glass polymer supports (see, e.g., Sarin et al., *Proc. Natl. Acad. Sci. USA* 85:7448-51

(1988)) (the disclosures of which are incorporated by reference herein), and the like. Other methods include those disclosed by Usman et al. (*J. Am. Chem. Soc.* 109:7845-54 (1987)), Scaringe et al. (*Nucleic Acids Res.* 18:5433-41 (1990)); Caruthers (*Oligonucleotides: Antisense Inhibitors of Gene Expression*, pp. 7-24, Cohen, (ed.), CRC Press, Inc. Boca Raton, Fla., 1989)); *Oligonucleotide Synthesis, A Practical Approach* (Gait (ed.), IRL Press, 1984); *Oligonucleotides and Analogues, A Practical Approach* (Eckstein, IRL Press, 1991); and in U.S. Pat. Nos. 4,415,732; 4,458,066; 4,500,707; 4,668,777; 4,973,679; 5,026,838; 5,132,418; and Re. 34,069. All of the foregoing references are incorporated by reference herein.

Small Molecule Effectors or Antagonists

Relaxin nucleic acids, polypeptides, analogs and fragments, and relaxin receptor nucleic acids, polypeptides, analogs and fragments and analogs, also have uses in screening assays to detect candidate compounds that specifically bind to relaxin polypeptides, or to relaxin receptor, and modulate apoptosis. Such candidate compounds are typically small molecule effectors (agonists) or antagonists, and can be identified by in vitro and/or in vivo assays. Such assays can be used to identify small molecule effectors or antagonists that are therapeutically effective as relaxin agonists or antagonists or as lead compounds for drug development. The invention thus provides assays to detect compounds that specifically affect the activity or expression of relaxin nucleic acids, relaxin polypeptides, relaxin receptor nucleic acids, relaxin receptor, and the like.

In a typical in vivo assay, recombinant cells expressing relaxin or relaxin receptor nucleic acids can be used to screen candidate compounds for those that affect relaxin or relaxin receptor nucleic acid expression. Agonistic or antagonistic effects on relaxin or relaxin receptor expression can include stimulation or inhibition (e.g., up or down regulation) of transcription of mRNA, a increase or decrease in mRNA stability, translation of the mRNA, synthesis of relaxin or relaxin receptor polypeptides, relaxin or relaxin receptor polypeptide function (e.g., binding to relaxin receptor), and/or effects on relaxin or relaxin receptor polypeptide stability or localization. Such effects on expression can be identified as physiological changes, such as, for example, changes in relaxin-responsive tissue growth rate, division, viability, collagen deposition, apoptosis, and the like. In one embodiment, candidate compounds are administered to recombinant cells expressing a relaxin or relaxin receptor polypeptide to identify those compounds that produce a physiological change (e.g., stimulate or inhibit relaxin or relaxin receptor polypeptide function).

Candidate compounds can also be identified by in vitro screening methods. For example, recombinant cells expressing a relaxin or a relaxin receptor nucleic acid can be used to recombinantly produce relaxin or relaxin receptor polypeptide for in vitro assays to identify candidate compounds that bind to relaxin or relaxin receptor polypeptide. Candidate compounds (such as small molecules) are contacted with the polypeptide (or a fragment or analog thereof) under conditions conducive to binding, and then candidate compounds that specifically bind to the polypeptide are identified. Methods that can be used to carry out the foregoing are commonly known in the art, and include diversity libraries, such as random or combinatorial peptide or non-peptide libraries that can be screened for candidate compounds that specifically bind to relaxin or relaxin receptor polypeptide. Many libraries are known in the art that can be used, for example, include chemically synthesized libraries, recombinant phage display libraries, and in vitro translation-based libraries.

Examples of chemically synthesized libraries are described in Fodor et al. (*Science* 251:767-73 (1991)), Houghten et al. (*Nature* 354:84-86 (1991)), Lam et al. (*Nature* 354:82-84 (1991)), Medynski (*BioTechnology* 12:709-10 (1994)), Gallop et al. (*J. Med. Chem.* 37(9):1233-51 (1994)), Ohlmeyer et al. (*Proc. Natl. Acad. Sci. USA* 90:10922-26 (1993)), Erb et al. (*Proc. Natl. Acad. Sci. USA* 91:11422-26 (1994)), Houghten et al. (*BioTechniques* 13:412-21 (1992)), Jayawickreme et al. (*Proc. Natl. Acad. Sci. USA* 91:1614-18 (1994)), Salmon et al. (*Proc. Natl. Acad. Sci. USA* 90:11708-12 (1993)), International Patent Publication WO 93/20242, and Brenner and Lerner (*Proc. Natl. Acad. Sci. USA* 89:5381-83 (1992)). (The disclosures of these references are incorporated herein.)

Examples of phage display libraries are described in Scott and Smith (*Science* 249:386-90 (1990)), Devlin et al. (*Science* 249:404-06 (1990)), Christian et al. (*J. Mol. Biol.* 227:711-18 (1992)), Lenstra (*J. Immunol. Meth.* 152:149-57 (1992)), Kay et al. (*Gene* 128:59-65 (1993)), and International Patent Publication WO 94/18318, the disclosures of which are incorporated by reference herein.

In vitro translation-based libraries include, but are not limited to, those described in International Patent Publication WO 91/05058, and Mattheakis et al. (*Proc. Natl. Acad. Sci. USA* 91:9022-26 (1994)). By way of examples of nonpeptide libraries, a benzodiazepine library (see, e.g., Bunin et al., *Proc. Natl. Acad. Sci. USA* 91:4708-12 (1994)) can be adapted for use. Peptide libraries (see, e.g., Simon et al., *Proc. Natl. Acad. Sci. USA* 89:9367-71(1992)) can also be used. Another example of a library that can be used, in which the amide functionalities in peptides have been permethylated to generate a chemically transformed combinatorial library, is described by Ostresh et al. (*Proc. Natl. Acad. Sci. USA* 91:11138-42 (1994)).

Screening the libraries can be accomplished by any of a variety of commonly known methods. See, for example, the following references, which disclose screening of peptide libraries: Parmley and Smith (*Adv. Exp. Med. Biol.* 251:215-18 (1989)); Scott and Smith (1990, supra); Fowlkes et al. (*BioTechniques* 13:422-28 (1992)); Oldenburg et al. (*Proc. Natl. Acad. Sci. USA* 89:5393-97 (1992)); Yu et al. (*Cell* 76:933-45 (1994)); Staudt et al. (*Science* 241:577-80 (1988)); Bock et al. (*Nature* 355:564-66 (1992)); Tuerk et al. (*Proc. Natl. Acad. Sci. USA* 89:6988-92 (1992)); Ellington et al. (*Nature* 355:850-52 (1992)); U.S. Pat. Nos. 5,096,815, 5,223,409, and 5,198,346; Rebar and Pabo (*Science* 263:671-73 (1994)); and International Patent Publication WO 94/18318, the disclosures of which are incorporated by reference herein.

In a specific embodiment, screening can be carried out by contacting the library members with relaxin, a relaxin analog, or a relaxin receptor immobilized on a solid phase and harvesting those library members that bind to the relaxin, relaxin analog or relaxin analog. Examples of such screening methods, termed "panning" techniques are described by way of example in Parmley and Smith (*Gene* 73:305-18 (1988)); Fowlkes et al. (1992, supra); International Patent Publication WO 94/18318; and in references cited herein.

Identifying a Subject with a Relaxin-Associated Abnormality

Relaxin nucleic acids (both sense and antisense), and fragments and analogs thereof, and anti-relaxin antibodies, also have utility to identify subjects with a relaxin-associated abnormality. Such molecules can be used in assays, such as hybridization or immunoassays, to detect, prognose, diagnose, or monitor various abnormalities, to determine whether relaxin expression, or the response to relaxin or a relaxin analog is affected. Similarly, such molecules have utility to monitor the treatment of the cell or tissue abnormalities. In particular, methods, such as an immunoassay, can be carried out by steps comprising contacting a sample derived from a subject with an anti-relaxin antibody under conditions conducive to immunospecific binding, and detecting or measuring the amount of any immunospecific binding of protein by the antibody. Binding of antibody to relaxin or relaxin receptor polypeptide, in tissue sections or from seminal fluid, can be used to detect aberrant (e.g., low, absent or elevated) levels of relaxin and/or relaxin receptor polypeptide. In a specific embodiment, antibody to relaxin or relaxin receptor polypeptide can be used to assay a subject's tissue or seminal fluid for the presence of relaxin or relaxin receptor polypeptide, where an aberrant level of relaxin is an indication of a relaxin-associated abnormality. By "aberrant levels" is meant increased or decreased levels relative to that present, or to a standard level representing that present, in an analogous sample from a portion of the body or from a subject not having the abnormality.

The immunoassays which can be used include, but are not limited to, competitive and non-competitive assay systems using techniques such as Western blot, radioimmunoassay, ELISA (enzyme linked immunosorbent assay), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, protein A immunoassay, and the like.

Relaxin and relaxin receptor nucleic acids (both sense and antisense), including fragments and analogs thereof, can also be used in hybridization assays. Such nucleic acids, comprising or consisting of at least contiguous 8 nucleotides, can be used as hybridization probes or for polymerase chain reaction detection. Hybridization assays can be used to detect, prognose, diagnose, or monitor diseases or conditions associated with aberrant relaxin or relaxin receptor expression and/or activity, as described supra. In particular, a hybridization assay can be carried out by a method comprising contacting a sample containing polynucleotides with a nucleic acid probe capable of hybridizing to relaxin or relaxin receptor DNA or RNA, under conditions such that hybridization can occur, and detecting or measuring any resulting hybridization.

In a specific embodiment, abnormalities associated with over- or under-expression of relaxin can be diagnosed, or their suspected presence can be screened for, or a predisposition to develop such abnormalities can be identified by detecting decreased or increased levels of relaxin polypeptide, relaxin RNA, or relaxin functional activity. Additionally, over-expression of relaxin or increased relaxin functional activity can be diagnosed by detecting mutations in relaxin RNA or DNA or relaxin polypeptide (e.g., translocations in relaxin nucleic acids, truncations of the relaxin gene or relaxin polypeptide, changes in the nucleotide or amino acid sequence relative to wild-type relaxin, respectively) that cause increased expression or activity of relaxin polypeptide.

By way of example, levels of relaxin polypeptide in a biopsy or from seminal fluid can be detected by immunoassay of tissues; levels of relaxin RNA can be detected by hybridization assays (e.g., Northern blot or dot blot). Translocations and point mutations in relaxin or relaxin receptor nucleic acids can be detected by Southern blot, RFLP analysis, PCR using primers that detect point mutations, deletions or insertions, sequencing of the relaxin genomic DNA or cDNA obtained from the sample, and the like.

In another embodiment, levels of relaxin or relaxin receptor mRNA or polypeptide in a sample of tissue isolated from a subject are detected or measured, in which increased levels indicate that the subject has, or has a predisposition to a relaxin-associated tissue abnormality.

In yet another embodiment, abnormal relaxin receptor activity in a tissue is detected or measured using any of the functional assays described above. Abnormal relaxin receptor activity can include, for example, an increased or decreased number of a relaxin receptors on relaxin-responsive cells, the presence of relaxin receptors on cells that are not normally responsive to relaxin, increased or decreased relaxin receptor response time, an increased or decreased binding affinity for relaxin or relaxin receptor, or a change in the dissociation constant of relaxin from a relaxin receptor, and the like.

Kits for diagnostic and/or prognostic use are also provided that comprise, in one or more containers, a relaxin agonist or antagonist and, optionally, a labeled binding partner to an antibody. Alternatively, an antibody can be labeled with a detectable marker (e.g., a chemiluminescent, enzymatic, fluorescent, a radioactive moiety, and the like). A kit is also provided that comprises, in one or more containers, a nucleic acid probe capable of hybridizing to relaxin or relaxin receptor mRNA or DNA.

In another embodiment, the kit can comprise in one or more containers a pair of primers (e.g., each in the size range of 6-30 nucleotides or more) that are capable of priming amplification (e.g., by polymerase chain reaction (see, e.g., Innis et al., *PCR Protocols*, Academic Press, Inc., San Diego, Calif. (1989)), ligase chain reaction (see, e.g., EP 0 320 308), use of Qβ replicase, cyclic 5' probe reaction, or other methods known in the art) under appropriate reaction conditions such that at least a portion of a relaxin nucleic acid is amplified. A kit can optionally further comprise in a container a predetermined amount of a purified relaxin or relaxin receptor nucleic acid, for example, for use as a standard or control.

The following examples are provided merely as illustrative of various aspects of the invention and shall not be construed to limit the invention in any way.

EXAMPLE 1

The effect of inactivation of one or both alleles of the mouse RLX genes was examined. The following methods and materials were followed.

Animals

Wild-type, heterozygous and homozygous relaxin knockout mice were obtained from the Howard Florey Institute of Experimental Physiology and Medicine (Parkville, Victoria, 3052, Australia) and used to establish a breeding program. Subsequent generations of RLX+/+ (wild-type), RLX+/− (heterozygous) and rlx−/− (null mutant) mice were generated from RLX+/− parents. All animals were housed in a controlled environment and maintained on a 14 hours light, 10 hours dark schedule with access to Labdiet rodent lab chow (Deans Animal Feed, San Bruno, Calif.) and water. These experiments were approved by the Institute's Animal Experimental Ethics Committee, which adheres to the NIH Code of Practice for the care and use of laboratory animals.

Genotyping by PCR

Mouse DNA was isolated by lysing tail tissue (5-7 millimeters) in 400 μl of PCR lysis buffer, containing 50 mM Tris-HCl, pH 8.0, 0.5% SDS, 0.1 M EDTA and 1 mg/ml proteinase K (Gibco BRL, Gaithersburg, Md.) at 50-55° C. overnight. Digested samples were then mixed with 3M sodium acetate (40 μl), buffer saturated phenol (200 μl) and chloroform (200 μl) in serum vaccutainer tubes, before samples were centrifuged at 3000 rpm for 10 minutes. The DNA (contained in the upper aqueous phase) was decanted into separate microcentrifuge tubes containing isopropyl alcohol (240 μl) to precipitate the DNA before samples were vortexed, spun and the supernatant discarded. The remaining DNA pellet was dissolved in 40-50 μl of sterile water. For PCR, each DNA template (1 μl) was used in a 30 μl reaction mixture containing PCR buffer (10 mM Tris-HCl, pH 8.3, 50 mM KCl, 1.5 mM $MgCl_2$), 2.5 mM dNTPs, 2.5 U Taq Polymerase (PGC Scientific, Gaithersburg, Md.) and 150 ng of each of the RLX+/+ and rlx−/− primers, designed by Zhao and colleagues (Zhao *Endocrinology* 140:445-53 (1999)). The amplification protocol consisted of an initial denaturation step at 94° C. (3 minutes) followed by 35 sequential cycles of 94° C. (60 seconds), 55° C. (60 seconds) and 72° C. (90 seconds) and concluded by an additional 10 minute extension at 72° C. 15 μl of each sample were then analyzed by electrophoresis on a 2% (w/v) agarose gel, and stained with ethidium bromide. A 235 bp product was generated by primers designed from the wild-type allele, while a 170 bp product was generated from the mutant allele primers (Zhao (1999), supra).

Tissue Collection and Histology

Relaxin wildtype, heterozygous and homozygous males and females (n≥20 in each of the 6 groups) were obtained at 1 week, 1 month, 2 months and 3 months of age and weighed. RLX+/+ and rlx−/− male mice were then sacrificed under anesthesia with carbon dioxide for tissue collection. The male reproductive tract (including testis, epididymis, prostate, seminal vesicle and attached fat) were collected from each animal at 1 week of age (n=10 RLX+/+ males, n=11−/− males); 1 month of age (n=10 RLX+/+ males, n=10−/− males); and 3 months of age (n=10 RLX+/+ males, n=10 rlx−/− males. After weighing each tissue, they were placed in 10% formalin for histological analysis.

The collected tissues were processed (sequentially dehydrated) from 70% alcohol to paraffin before being embedded and cut (4 μm sections), using an AO Spencer 820 microtome and placed on poly-L-lysine coated glass slides. Consecutive sections from each tissue were stained with H & E (hematoxylin and eosin) and for collagen, with Masson trichrome (staining kit, Richard-Allan Scientific®, Kalamazoo, Mich.) as described by the manufacturer. The stained slides were viewed using a Zeiss Axioplan-2® microscope, the images captured by digital camera (Hamamatsu) and stored for retrieval and analysis. The images were digitally enhanced for maximum contrast and brightness using Adobe Photoshop (Adobe Systems® Inc, Mountain View, Calif.).

Antibody Staining of Paraffin-Embedded Tissue Sections

The tissues from the reproductive tract of one and three month old male mice were mounted on precoated slides and deparaffinized by heating at 58° C. (about 30 minutes), then washed three times in xylene, twice in absolute ethanol and twice in 95% ethanol, before being briefly soaked in water. The samples were then stained using an Immunocruz® staining system utilizing a horseradish peroxidase (HRP)-streptavidin complex (Santa Cruz Biotechnology®, Inc, Santa Cruz, Calif.) in a humidified atmosphere. Tissue sections were initially treated with a peroxidase blocker (to quench endogenous peroxidase activity) (5 minutes) before being preblocked in goat serum (20 minutes). Serial sections from each RLX+/+ and rlx−/− tissue sample were then incubated with either a Bax monoclonal IgG primary antibody (4 μg/ml) (Santa Cruz Biotechnology®, Inc), a caspase-9 polyclonal IgG antibody (4.5 μg/ml) (Santa Cruz Biotechnology®, Inc.) or a proliferating cell nuclear antigen (PCNA) (Santa Cruz Biotechnology® Inc.) monoclonal IgG antibody (4 μg/ml) (2 hours). Depending on the type of antibody used, either a mouse IgG or rabbit IgG control (Santa Cruz Biotechnology®, Inc.) stain of tissues (2 hours) was also used in all experiments performed. Samples were washed in PBS (2 minutes), subjected to the appropriate secondary antibody (goat anti-mouse IgG or goat anti-rabbit IgG) (30 minutes), washed as above (2 minutes), treated with a HRP-streptavidin complex (30-45 minutes) and incubated with a diaminobenzidine chromagen substrate (2-10 minutes) that was prepared in accordance with the manufacturer's instructions. The slides were then washed in distilled water (2 minutes) before being dehydrated from 95% alcohol to xylene and mounted, then photographed as described above.

Statistical Analysis

The results were analyzed using a one-ANOVA test. All data in this paper are presented as the mean±SEM, with $p<0.05$ considered statistically significant.

EXAMPLE 2

The Effects of Relaxin Gene Knockout on the Growth of Mice

The body weights of male and female relaxin wildtype (+/+), heterozygous (+/−) and null mutant (−/−) mice were measured at 1 week, 1 month, 2 months and 3 months of age (n=20-21 for each group). No significant differences in mean body weight were noted in male (RLX+/+: 3.87±0.09 g; rlx−/−: 3.6±0.13 g) or female (RLX+/+: 3.52±0.09 g; rlx−/−: 3.37±0.08 g) mice at 1 week of age. However, at the time the mice were 1 month of age, mean body weights of both rlx−/− males (17.05±0.65 g) and females (14.77±0.42 g) were significantly less ($p<0.05$) than their respective RLX wild-type counterparts (RLX+/+ M: 18.92±0.61 g; RLX+/+ F: 16.34±0.51 g). Male and female null mutant mice continued to be significantly smaller ($p<0.05$) than RLX wildtype animals at 2 months of age (RLX+/+ M: 25.42±0.41 g; rlx−/− M: 24.23±0.42 g; RLX+/+ F: 20.96±0.32 g; rlx−/− F: 19.94±0.22 g); however, the differences in size between the two groups were less than that observed at 1 month of age. By adulthood (3 months of age), the mean weight of rlx−/− mice (rlx−/− M: 26.57±0.47 g; rlx−/− F: 22.54±0.31 g) was still slightly less than the average weight of adult RLX+/+ mice (RLX+/+ M: 27.30±0.32 g; RLX+/+ F: 23.03±0.71 g), but this difference was no longer significant. The mean weight of the RLX+/− mice was between that of the average weight of RLX+/+ and rlx−/− mice. No significant differences were observed between the average weight of RLX+/+ and RLX+/− animals, or between RLX+/− and rlx−/− mice.

The Effects of Relaxin Gene Knockout on the Size of the Male Reproductive Tract No significant difference was observed in the weight or size of the male reproductive tract at 1 week of age, which was represented primarily by the testis (Table 1). By 1 month of age the collected male genital tract was composed of the testis, epididymis, prostate, seminal vesicle, ductus deference and attached fat. Although no difference in the overall weight of the reproductive tract was observed at one month of age, differences in size of the testis and prostate, derived from 1 month null mutant mice, were approximately 20% and 30% smaller, respectively, than the corresponding tissues of RLX wildtype animals, while the size of the epididymis, derived from rlx−/− mice was significantly ($p<0.05$) smaller than that obtained from RLX+/+ animals. No differences were noted, however, in the size of the seminal vesicle between tissue samples collected from RLX+/+ and rlx−/− mice.

By the time the mice had reached adulthood (3 months of age), a significant ($p<0.05$) difference in the overall weight of the male reproductive tract as well as in the size of individual organs was observed (Table 1). The weight of the reproductive tract in normal mice increased 248.6% from 1 month to adulthood and represented 3.37% of the total body weight. During this time, the weight of the reproductive tract from male RLX null mutant mice only increased by 187.9% and represented 2.33% of the total body. This latter finding implied that the reproductive tract of male rlx−/− mice represented a 31% decrease in % body weight. The size of the testis, epididymis, prostate and seminal vesicle from rlx−/− mice were all smaller ($p<0.05$) than their respective counterparts, derived from RLX+/+ mice.

TABLE 1

The weight and size of the male reproductive tract from 1 week of age to adulthood (6.5 months).

| | RLX +/+ [Mean ± SE(n)] | % of Body Weight | rlx −/− [Mean ± SE(n)] | % of Body Weight |
|---|---|---|---|---|
| 1 Week of Age: | | | | |
| Weight (g): | | | | |
| Overall | 0.017 ± 0.001(10) | 0.43 | 0.018 ± 0.002(15) | 0.53 |
| Size (Area; mm$^2$): | | | | |
| Testis | 1.30 ± 0.30 (5)[1] | — | 1.41 ± 0.23 (5)[1] | — |
| 1 Month of Age: | | | | |
| Weight (g): | | | | |
| Overall | 0.37 ± 0.02(11) | 1.81 | 0.33 ± 0.01 (11) | 1.77 |
| Size (Area; mm$^2$): | | | | |
| Testis | 16.36 ± 1.58 (9)[1] | — | 12.91 ± 0.96 (8)[1] | — |
| Epididymis | 10.73 ± 2.22 (7)[2] | — | 4.62 ± 0.64 (7)[2]* | — |
| Prostate | 9.20 ± 1.20 (4)[3] | — | 6.30 ± 0.54 (4)[3] | — |
| Seminal Vesicle | 1.50 ± 0.25 (4)[4] | — | 1.69 ± 0.22 (4)[4] | — |
| 3 Months of Age: | | | | |
| Weight (g): | | | | |
| Overall | 0.92 ± 0.06(14) | 3.37 | 0.62 ± 0.03 (11)* | 2.33 |
| Size (Area; mm$^2$): | | | | |
| Testis | 27.21 ± 1.52 (12)[1] | — | 17.31 ± 2.28 (10)[1] | — |
| Epididymis | 23.62 ± 3.19 (11)[2] | — | 13.71 ± 2.74(10)[2]* | — |
| Prostate | 20.89 ± 1.20 (6)[3] | — | 15.03 ± 1.60 (6)[3]* | — |
| Seminal Vesicle | 25.75 ± 3.58 (7)[4] | — | 14.6 ± 2.88 (5)[4]* | — |

The size of each [1] testis and [3] prostate was measured by its area, multiplying the tissue length by width. The size (area) of the epididymis and seminal vesicle could not be measured accurately, so a close approximation of each tissue was calculated as follows: epididymis (by measuring the length of the tissue by the width of the epididymis head[2]); seminal vesicle (by measuring the length of each organ by the average width of the tissue[4]).
*denotes $p < 0.05$.

The Effects of Relaxin Gene Knockout on Histology of the Male Reproductive Tract H&E & Masson Trichrome Staining: Male reproductive tissue sections from RLX+/+ and rlx−/− mice, were first observed for differences in sperm maturation, tubule size/compactness (testis, epididymis) and collagen.

Testis: At 1 week of age, the seminiferous tubules (the compartments containing germ cells/spermatocytes, Sertoli cells and where sperm maturation occurs) of relaxin wildtype animals were smaller, more cylindrical in shape (Table 2) and mainly supported by a thin layer of collagen surrounding the tunica albuginea (the membrane that covers the oval body) of each organ. In comparison, tubules derived from rlx−/− mouse testes were much larger and elongated, but were completely surrounded and supported by collagen within the testis. This immediately suggested a difference in the internal organization of the testis in the absence of relaxin, even just after birth. No immature sperm though were detected in either group of tissue sections at one week of age. By one month of age, testis tubules derived from RLX+/+ mice were larger in size (compared to 1 week tubule size), were slightly less compact and contained mainly immature sperm. In comparison, the tubules derived from 1 month old RLX homozygous mice were no different to tubule sizes measured from 1 week old knockout mice and contained less immature sperm compared to samples derived from RLX+/+ mice. This further suggested that relaxin null mutant mice were undergoing a process of delayed sperm maturation which was further confirmed when comparing three month tissue sections; sections derived from RLX+/+ mouse tissues contained larger tubules (compared to 1 month tubule size) with mainly mature sperm. Conversely, sections derived from rlx−/− mice contained slightly smaller tubules (which were indifferent to tubule sizes derived from 1 week/1 month rlx−/− mice) with less mature sperm (compared to 3 month RLX+/+ tissue sections) and still some immature sperm. The level of sperm maturity in testes derived from RLX+/+ mice was shown to be significantly ($p<0.05$) greater than the level of sperm maturation observed in the testes of rlx−/− mice (see Table 2 for grading scale used). It was also noted that the level of sperm maturation in adult RLX knockout mouse testes resembled that observed in immature (1 month) RLX wildtype mouse tissues. From 1-3 months of age, the testis of normal mice continued to be surrounded by a thin layer of collagen, covering the tunica albuginea; however, in some tissues a scattered thin lining of collagen was also observed to support the seminiferous tubules. The internal layering of collagen though, was found to decrease with age. In rlx−/− mice, the collagen detected in-between tubular structures had regressed due to the larger tubular sized structures within the testis, but was still more dense and consistent compared to that observed in tissue samples derived from wildtype animals. It is postulated that the increased collagen observed in the reproductive tract of RLX null mutant mice at a very young age may cause tissues to be more rigid and firm, which may be linked to the changes in tubular composition and sperm maturation that are discussed above. Interestingly, the presence of relaxin in normal adult mice also induced a loosening (increased interstitial spacing) of the seminiferous testis tubular structures compared to that observed from normal immature (1 month) mice. In comparison, there was no difference in tubule organization (size/compactness) from testes derived from 1 month and 3 month rlx−/− mice. Additionally, 1 month, and to an extent 3 month, testis tubules derived from rlx−/− mice appeared to contain an increased number of dead cells, compared to tubular cells derived from RLX wildtype animals. The increased number of dead cells seen in immature tissues were variable between animals but were consistently detected as the mice matured with age.

Epididymis: No significant differences in tubule size were noted in the epididymis of RLX+/+ and rlx−/− reproductive tracts at 1 month and 3 months of age. By adulthood however, tubule compactness was more evident in tissues derived from RLX homozygous mice as compared to tissues derived from RLX wildtype animals. The epididymis tubules of rlx−/− mice were also supported to a greater extent by connective tissue. Tubular structures derived from 3 month RLX+/+ mouse tissues were loose and only partially maintained by collagen. Conversely, tissue sections obtained from RLX knockout animals were shown to have more compact tubules that were fairly well enclosed by thin layers of collagen. As in the case of the testis, tissues obtained from rlx −/− mice were upheld by an increased concentration of collagen, at all ages observed, compared to tissue samples derived from RLX+/+ mice. As shown in Table 2, it was also noted that the density of mature sperm (in epididymis tubules) was less in tissue sections derived from RLX null mutant mice at 1 month and 3 months of age, compared to that obtained from RLX wildtype mice, at each respective age group. This difference, however, was statistically insignificant. This decrease in mature sperm in the epididymis of mice lacking relaxin was most likely attributed to the delayed sperm maturation process that took place in the testis of these animals (Table 2).

TABLE 2

The effects of relaxin gene knockout on tissue compartment and sperm maturation, during murine growth and development

| Tissue | Age [months] | RLX +/+ [Mean ± SE (n)] | rlx −/− [Mean ± SE (n)] |
|---|---|---|---|
| Testis: | | | |
| Tubule size[a] | [0.23] | 2.20 ± 0.32 (5) | 2.60 ± 0.20 (5) |
|  | [1] | 2.92 ± 0.17 (9) | 2.70 ± 0.13 (8) |
|  | [3] | 3.64 ± 0.08 (9) | 2.86 ± 0.18 (10)* |
|  | [6.5] | 3.17 ± 0.17 (3) | 3.08 ± 0.08 (3) |
| Tubule compactness[b] | [0.23] | 3.90 ± 0.10 (5) | 3.45 ± 0.20 (5) |
|  | [1] | 3.56 ± 0.15 (9) | 2.66 ± 0.32 (8) |
|  | [3] | 1.75 ± 0.28 (9) | 2.60 ± 0.17 (8)* |
|  | [6.5] | 2.33 ± 0.08 (3) | 3.66 ± 0.09 (4)* |
| Sperm maturation[c] | [0.23] | 0 (5) | 0 (5) |
|  | [1] | 1.78 ± 0.36 (9) | 0.94 ± 0.20 (8) |
|  | [3] | 3.78 ± 0.15 (9) | 2.20 ± 0.29 (10)* |
|  | [6.5] | 3.75 (3) | 3.56 ± 0.12 (4) |
| Epididymis: | | | |
| Tubule size[a] | [1] | 2.48 ± 0.24 (7) | 2.74 ± 0.36 (7) |
|  | [3] | 2.47 ± 0.22 (8) | 2.92 ± 0.23 (7) |
|  | [6.5] | 2.67 ± 0.17 (3) | 2.88 ± 0.13 |
| Tubule compactness[b] | [1] | 3.16 ± 0.28 (7) | 3.01 ± 0.25 (7) |
|  | [3] | 2.68 ± 0.28 (8) | 3.24 ± 0.28 (7) |
|  | [6.5] | 2.33 ± 0.44 (3) | 3.00 ± 0.18 (4) |
| Sperm maturation[c] | [1] | 0.94 ± 0.06 (8) | 0.75 ± 0.10 (8) |
|  | [3] | 3.56 ± 0.13 (9) | 3.05 ± 0.17 (10) |
|  | [6.5] | 3.83 ± 0.08 (3) | 3.63 ± 0.07 (4) |

Table 2: Tissue sections were stained with H & E and graded as follows:
[a]Tubule size - 1 = all tubules small and circular in shape; 2 = most tubules slightly elongated compared to 1 but some smaller circular tubules are observed; 3 = tubules grossly elongated compared to 1, but some smaller circular and mid-sized tubules are observed; 4 = all tubules grossly elongated compared to 1 and 2.
[b]Tubule compactness - 1 = all tubules loose; 2 = proportion of loose tubules greater than proportion of compact tubules; 3 = proportion of compact tubules greater than proportion of loose tubules; 4 = all tubules compact.
[c]Sperm maturation - 0 = no sperm detected; 1 = only immature sperm detected; 2 = proportion of immature sperm greater than proportion of mature sperm; 3 = proportion of mature sperm greater than proportion of immature sperm; 4 = only mature sperm detected. The numbers presented are the mean ± SE (n) of the grading scale used for each parameter measured.
*denotes $p < 0.05$.

TABLE 3

The effects of relaxin gene knockout on collagen maturation, during murine growth and development

| Tissue | Age [months] | RLX +/+ [Mean ± SE (n)] | rlx −/− [Mean ± SE (n)] |
|---|---|---|---|
| Testis[a]: | [0.23] | 1 (4) | 2.00 ± 27 (4) |
|  | [1] | 1.09 ± 0.07 (8) | 1.61 ± 0.25 (7) |
|  | [3] | 1.06 ± 0.06 (9) | 1.28 ± 0.09 (8) |
|  | [6.5] | 1.75 ± 0.14 (3) | 2.31 ± 0.12 (4) |
| Epididymis[a]: | [1] | 2.41 ± 0.33 (7) | 2.57 ± 0.39 (7) |
|  | [3] | 1.82 ± 0.21 (8) | 2.86 ± 0.29 (8)* |
|  | [6.5] | 2.92 ± 0.08 (3) | 3.06 ± 0.19 (4) |
| Prostate[a]: | [1] | 1 (3) | 2.33 ± 0.17 (3) |
|  | [3] | 1.25 ± 0.17 (6) | 2.25 ± 0.28 (6) |
|  | [6.5] | 1.5 (3) | 2.69 ± 0.37 (4)* |
| Seminal Vesicle[a]: | [1] | 1 (3) | 1.50 ± 0.25 (4) |
|  | [3] | 1.14 ± 0.09 (7) | 1.70 ± 0.19 (5) |

Table 3: Tissue sections were stained with Masson trichrome stain and graded as follows:
[a]Collagen - 1 = only thin lining of collagen surrounding the outer layer of structures; 2 = additional lining of collagen surrounding internal components of tissue; 3 = thicker lining of collagen surrounding outer layer and internal components of tissues; 4 = 3 + spacing between tubules/components filled with collagen.
The numbers presented are the mean ± SE (n) of the grading scale.
*denotes $p < 0.05$ Prostate: At 1 month of age, no significant differences were noted in the structure of the prostate between RLX+/+ and rlx−/− derived tissues. However, the spacing between the ducts of prostate glands from normal animals was associated with only trace amounts of collagen. In contrast, the ducts of prostate glands from rlx−/− mice were intervened by layers of loose connective tissue. By adulthood (3 months), rlx−/− mice contained smaller prostates with smaller glands and ducts. The ducts of tissues derived from RLX knockout mice were more compact and completely supported by connective tissue, while the ducts obtained from RLX wildtype mice were more spread out (loose) and still supported by little collagen. Furthermore, the ducts of the adult prostate obtained from rlx−/− mice appeared to have smaller epithelium, containing less cells, while the ducts of RLX+/+ prostate samples contained larger epithelial layers/glandular tissue. These results added to our initial findings on the testis and epididymis in implying that a delayed maturation process of male reproductive tissues was taking place in mice lacking a functionally active relaxin gene and involved an accumulation of collagen within these tissues.

Detection of Cell Apoptosis by Antibody Staining:

Based on observations made from H&E staining, whereby tissues derived from rlx−/− mice underwent decreased sperm maturation and increased cell death (testis) and contained decreased epithelial (cell) layers (prostate), it was decided to investigate whether the increased cell death observed were the result of apoptotic pathways.

Bax Antibody Staining: Overexpression of Bax accelerates apoptotic death induced by cytokine deprivation and also counters the death repressor activity of Bcl-2 (Krajewski et al., *Am. J. Pathol.* 145:1323-36 (1994)). Using a Bax monoclonal antibody, the in vivo distribution of the Bax protein was evaluated in the male reproductive tract. Testis: Seminiferous tubules derived from immature (1 month) wildtype animals showed weak immunostaining for Bax (dark brown cell staining), which was primarily observed in the germinal cells near the basement membrane. These findings are consistent with those of previous reports (Ben-Hur et al., *Calcif. Tiss. Int.* 53:91-96 (1996)). In comparison, an increased number of cells were stained positive for Bax in testes derived from rlx−/− mice. The number of Bax positive cells were counted using a hemacytometer and shown to be significantly greater in the testis of rlx−/− mice (32.7±4.8 cells/testis (n=6)) compared to the number of apoptotic cells observed from RLX+/+ mouse-derived tissues (13.1±3.5 cells/testis (n=6)). While increased Bax staining was consistently observed in rlx−/− tissues, the number of tubules stained positive for Bax varied between tissue samples, and some tubules were also observed to be Bax-free. As the male reproductive tract matured, adult RLX wildtype mice testes showed decreased staining for Bax (3.4±1.4 cells/testis (n=6)) which correlated with the increased level of sperm and tissue maturity that these animals underwent. Conversely, the slower rate of tissue maturity observed in the rlx−/− mouse reproductive tract correlated with a further increase in Bax staining in 3 month RLX knockout mice (44.4±8.1 cells/testis (n=6)). Many of the observed cells appeared to be at the final stages of apoptosis, perhaps representing apoptotic bodies. Bax staining was not associated with mature sperm cells though. Epididymis: A more intense Bax staining was present in the intracellular membrane of epithelial cells of epididymis tubules derived from 1 month RLX+/+ mouse tissues. The same tubules derived from 1 month rlx−/− mouse tissues contained a relatively stronger level of Bax staining, which was further maintained, if not increased in 3 month tissue sections. In contrast, the epididymis of adult wildtype mice contained a weaker expression of Bax staining, compared to tissues derived from 1 month normal mice, as the tissue matured with age. Prostate: The epithelial cells of the prostate of normal 1 month and 3 month animals showed weak positive staining for Bax. As with the other tissues studied, cells specifically within the epithelial layer (of prostate ducts) of rlx−/− animals showed increased staining for Bax in both immature (1 month) and adult (3 month) tissues. These findings suggested that relaxin may have played a novel role in the regulation of cell apoptosis within the male reproductive tract, however, further work using a separate antibody to detect cell apoptosis was conducted to confirm the actions of relaxin.

Caspase-9, a central death protease, belongs to a unique family of cysteine proteases that differ in sequence, structure and substrate specificity to other described protease families. The caspase family members (which are usually involved in a cascade of proteolytic cleavage events) function as key components of the apoptotic machinery by acting to destroy specific target proteins which are critical to cellular activity. Testis:

Moderate caspase-9 staining was observed in 1 month RLX+/+ testes (28.1±5.6 cells/testis (n=7)), which appeared to be primarily associated with the germinal cells within the seminiferous tubules, rather than with spermatagonia or spermatocytes. As with Bax, a significantly ($p<0.05$) increased level of caspase-9 staining was detected in 1 month rlx−/− mouse testes (76.6±10.2 cells/testis (n=6)), although heavy caspase-9 staining was associated with few tubules, while many tubules were observed to contain little or no caspase-9 protein. With age, the level of caspase-9 detected in normal immature tissues was consistently found in older tissues at 3 months of age (26.9±4 cells/testis (n=6)). However, as the testis increased in size, the number of apoptotic cells detected represented a smaller fraction of the tissue with age. Testis tubules derived from rlx−/− mice contained slightly fewer apoptotic cells at 3 months (61.6±9.8 cells/testis (n=5)), compared to the density of caspase-9 stained cells in 1 months tissues. The number of positively stained apoptotic cells from RLX knockout mouse tissues though, remained significantly ($p<0.05$) greater than their wildtype counterparts at all ages studied. Epididymis: No staining for caspase-9 was detected from 1 month RLX+/+ epididymis tubules, while trace amounts of positive cells were observed in rlx−/− tissue sections. However, the positively stained cells were sparsely scattered and were detected in the epithelial layer of the tubules. With age, clear staining for caspase-9 was not detected in 3 month RLX+/+ and rlx−/− mouse tissues. Prostate: No staining for caspase-9 was identified in the prostate of RLX+/+ and rlx−/− tissues at all ages (1-3 months) investigated. Nevertheless, the obtained results suggested for the first time, that relaxin is linked to the regulation of cell apoptosis. Additional work though was required to establish whether relaxin was involved in cell proliferation pathways.

Detection of Cell Proliferation by Antibody Staining:

PCNA staining: The proliferating cell nuclear antigen (PCNA) antibody was used to detect cell proliferation in the male reproductive tract based on its ability to associate with nuclear regions where DNA synthesis is occurring. Testis: PCNA was detected in immature and mature seminiferous tubules, although no significant differences in PCNA staining were detected in testis tubules derived from RLX+/+ and rlx−/− mice at 1 month and 3 months of age. In immature tissues, PCNA staining is usually highly expressed in mitotically active spermatogonia and occasionally in some Sertoli cells, which corresponds to proliferative activity. In this study, these cells were more uniformly and continuously labeled for PCNA even well into murine adulthood, which perhaps reflects the ability of both groups to be able to initiate reproduction, via the constant activation of these proliferative cells. Epididymis: No staining for PCNA was detected in the epididymis derived from either RLX+/+ or rlx−/− mice at 1 month and 3 months of age. These findings are consistent with the role of the epididymis in acting as a reservoir for mature sperm. Prostate: Weak staining for PCNA was associated with the epithelial cells of prostate ducts derived from 1 month RLX+/+ and rlx−/− mice. However, no staining for PCNA was detected from either group at 3 months of age. While cell proliferation studies were limited to some reproductive tissues, the accumulated findings perhaps confirmed that relaxin was most likely to play an influential role in the regulation of cell apoptosis, rather than on cell proliferation.

The Effects of Relaxin Gene Knockout on Histology of Other Body Tissues

RLX wildtype (RLX+/+) and RLX gene knockout (rlx−/−) male and female mice were generated from RLX heterozygous (RLX+/−) parents, as described above. Mice were weighed and sacrificed at 1 week, 1 month and 3 months of age for tissue collection. The following tissues, including the brain, heart, liver, kidneys, thymus, spleen and male reproductive tract were collected, weighed and placed into 10% formalin for detailed histological analysis. A summary of the weights of these tissues are shown in Tables 4-8.

At 1 week of age, male rlx−/− mice contained significantly ($p<0.05$) smaller livers, kidneys and spleens compared to RLX+/+ animals, but these weight differences were no longer apparent at 1 month of age. Instead, the thymus of 1 month old rlx−/− male mice was smaller ($p<0.05$) than their RLX+/+ counterparts. This weight difference was no longer apparent at 3 months of age. In the case of the male reproductive tract, no significant differences were noted at 1 week or 1 month of age between RLX+/+ and rlx−/− groups, however by 3 months of age, the reproductive tract of rlx−/− mice was significantly ($p<0.05$) smaller than that obtained from RLX+/+ animals.

No notable differences were observed between 1 week old RLX+/+ and rlx−/− female mice, however, by 1 month of age, rlx−/− female mice had significantly smaller livers than their RLX+/+ counterparts. By three months of age, this weight difference was no longer observed and no other significant differences of the other organs were noted.

To determine if the organ and tissue differences in RLX−/− mice (derived from RLX+/− parents) would be accentuated further if rlx−/− offspring were obtained from RLX−/− parents, RLX+/+ and rlx−/− mice ere obtained from the corresponding set of parents and were sacrificed at 1 week, 1 month and 3 months of age. The brain, heart, liver, kidneys, thymus, spleen, male reproductive tract, intestine and lung were collected and weighed. The weights of these organs are shown in Tables 4-8.

It was further noted that, although the weights of organ or tissue appeared to normalize as the mice become older, normal weight alone does not equate with a normal organ or tissue. The data show that a discrepancy in organ (tissue) weight to body weight ratio at any time in the growth cycle indicates a change in underlying organ or tissue development or cellular architecture. As one example, a small liver that is infiltrated (altered) by fibrosis will weigh the same or more than a larger normal liver or one filled with fat. Thus, tissues from brain, heart, liver, kidneys, thymus, spleen, intestine and lung of male and female RLX−/− mice (developed in the absence of relaxin) show evidence of increased apoptosis and extracellular matrix (collagen) accumulation.

TABLE 4

Tissue Comparison of 1 week old (from RLX +/+ & rlx −/− parents, respectively), Represented as Mean ± SE (n):

|  | RLX +/+ Male | % body wt | rlx −/− Male | % body wt |
|---|---|---|---|---|
| Body wt (g) | 3.85 ± 0.14 (10) | — | 3.32 ± 0.14 (15) | — |
| Rep. Organ (g) | 0.017 ± 0.001 (10) | 0.43 | 0.018 ± 0.001 (15) | 0.53 |
| Brain (g) | 0.24 ± 0.01 (10) | 6.31 | 0.21 ± 0.01 (15) | 6.40 |
| Heart (g) | 0.023 ± 0.002 (10) | 0.58 | 0.020 ± 0.001 (15) | 0.60 |
| Liver (g) | 0.12 ± 0.01 (10) | 3.13 | 0.094 ± 0.01 (15)* | 2.82 |
| L. Kidney (g) | 0.023 ± 0.001 (10) | 0.59 | 0.018 ± 0.001 (15)* | 0.54 |
| R. Kidney (g) | 0.023 ± 0.001 (10) | 0.59 | 0.019 ± 0.001(15)* | 0.56 |
| Spleen (g) | 0.033 ± 0.002 (10) | 0.59 | 0.018 ± 0.001 (15)* | 0.54 |
| Thymus (g) | 0.020 ± 0.001 (10) | 0.51 | 0.018 ± 0.001 (15) | 0.54 |

|  | RLX +/+ Female | % body wt | rlx −/− Female | % body wt |
|---|---|---|---|---|
| Body wt (g) | 3.45 ± 0.19 (9) | — | 3.51 ± 0.15 (9) | — |
| Brain (g) | 0.22 ± 0.01 (9) | 6.23 | 0.22 ± 0.01 (9) | 6.11 |
| Heart (g) | 0.023 ± 0.002 (9) | 0.67 | 0.02 ± 0.001 (9) | 0.57 |
| Liver (g) | 0.085 ± 0.01 (9) | 2.46 | 0.10 ± 0.01 (9) | 2.85 |
| L. Kidney (g) | 0.019 ± 0.001 (9) | 0.55 | 0.20 ± 0.001 (9) | 0.56 |
| R. Kidney (g) | 0.020 ± 0.001 (9) | 0.57 | 0.20 ± 0.001 (9) | 0.57 |
| Spleen (g) | 0.020 ± 0.002 (9) | 0.57 | 0.017 ± 0.002 (9) | 0.48 |
| Thymus (g) | 0.017 ± 0.002 (9) | 0.48 | 0.017 ± 0.001 (9) | 0.47 |

*=> $p < 0.05$

TABLE 5

Tissue Comparison 1 month old mice (from RLX+/− parents), Represented as Mean ± SE (n):

|  | RLX +/+ Male | % body wt | rlx −/− Male | % body wt |
|---|---|---|---|---|
| Body wt (g) | 20.54 ± 0.82 (10) | — | 18.29 ± 0.84 (10) | — |
| Rep. Organ (g) | 0.37 ± 0.02 (11) | 1.81 | 0.33 ± 0.01 (11) | 1.78 |
| Brain (g) | 0.37 ± 0.01 (10) | 1.81 | 0.37 ± 0.01 (10) | 2.03 |
| Heart (g) | 0.13 ± 0.004 (10) | 0.62 | 0.13 ± 0.01 (10) | 0.69 |
| Liver (g) | 1.17 ± 0.05 (10) | 5.70 | 1.10 ± 0.05 (10) | 5.99 |
| L. Kidney (g) | 0.16 ± 0.01 (10) | 0.77 | 0.14 ± 0.01 (10) | 0.78 |
| R. Kidney (g) | 0.17 ± 0.01 (10) | 0.82 | 0.14 ± 0.01 (10) | 0.78 |
| Spleen (g) | 0.12 ± 0.01 (10) | 0.57 | 0.12 ± 0.01 (10) | 0.66 |
| Thymus (g) | 0.06 ± 0.01 (10) | 0.28 | 0.075 ± 0.005 (10) | 0.41 |

|  | RLX +/+ Female | % body wt | rlx −/− Female | % body wt |
|---|---|---|---|---|
| Body wt (g) | 16.93 ± 0.45 (10) | — | 16.04 ± 0.61 (9) | — |
| Brain (g) | 0.36 ± 0.01 (9) | 2.14 | 0.36 ± 0.01 (9) | 2.23 |
| Heart (g) | 0.09 ± 0.003 (10) | 0.53 | 0.10 ± 0.003 (9) | 0.60 |
| Liver (g) | 0.90 ± 0.02 (10) | 5.32 | 0.78 ± 0.02 (9)* | 4.84 |
| L. Kidney (g) | 0.13 ± 0.005 (10) | 0.78 | 0.12 ± 0.003 (9) | 0.76 |
| R. Kidney (g) | 0.13 ± 0.004 (10) | 0.78 | 0.13 ± 0.01 (9) | 0.80 |
| Spleen (g) | 0.08 ± 0.004 (10) | 0.45 | 0.08 ± 0.01 (9) | 0.50 |
| Thymus (g) | 0.07 ± 0.01 (10) | 0.39 | 0.07 ± 0.01 (9) | 0.42 |

*=> $p < 0.05$

TABLE 6

Tissue Comparison of 3 month old male mice (from RLX +/+ & rlx −/− parents, respectively), Represented as Mean ± SE (n):

| | RLX +/+ Male | % body wt | rlx −/− Male | % body wt |
|---|---|---|---|---|
| Body wt (g) | 27.41 ± 0.39 (14) | — | 26.57 ± 0.51 (11) | — |
| Rep. Organ (g) | 0.92 ± 0.06 (14) | 3.37 | 0.62 ± 0.02 (11) | 2.33 |
| Brain (g) | 0.37 ± 0.01 (10) | 1.34 | 0.37 ± 0.01 (10) | 1.40 |
| Heart (g) | 0.15 ± 0.003 (10) | 0.56 | 0.14 ± 0.01 (10) | 0.54 |
| Liver (g) | 1.32 ± 0.08 (10) | 4.80 | 1.28 ± 0.04 (10) | 4.82 |
| L. Kidney (g) | 0.24 ± 0.01 (10) | 0.87 | 0.21 ± 0.01 (10) | 0.81 |
| R. Kidney (g) | 0.23 ± 0.01 (10) | 0.83 | 0.22 ± 0.01 (10) | 0.82 |
| Spleen (g) | 0.08 ± 0.01 (10) | 0.29 | 0.08 ± 0.003 (10) | 0.29 |
| Thymus (g) | 0.056 ± 0.01 (10) | 0.20 | 0.051 ± 0.003 (10) | 0.19 |

| | RLX +/+ Female | % body wt | rlx −/− Female | % body wt |
|---|---|---|---|---|
| Body wt (g) | 23.14 ± 1.08 (10) | — | 21.62 ± 0.39 (9) | — |
| Brain (g) | 0.38 ± 0.01 (10) | 1.64 | 0.39 ± 0.01 (9) | 1.80 |
| Heart (g) | 0.10 ± 0.004 (10) | 0.44 | 0.11 ± 0.004 (9) | 0.49 |
| Liver (g) | 1.07 ± 0.05 (10) | 4.61 | 1.01 ± 0.004 (9) | 4.66 |
| L. Kidney (g) | 0.16 ± 0.004 (10) | 0.67 | 0.15 ± 0.006 (9) | 0.69 |
| R. Kidney (g) | 0.16 ± 0.005 (10) | 0.70 | 0.15 ± 0.003 (9) | 0.70 |
| Spleen (g) | 0.09 ± 0.01 (10) | 0.37 | 0.09 ± 0.01 (9) | 0.41 |
| Thymus (g) | 0.06 ± 0.003 (10) | 0.26 | 0.06 ± 0.003 (9) | 0.29 |

*=> $p < 0.05$

TABLE 7

Tissue Comparison of 1 month old mice (from RLX+/+ and RLX−/− parents, respectively), represented as Mean ± SE (n):

| | RLX +/+ Male | % body wt | rlx −/− Male | % body wt |
|---|---|---|---|---|
| Body wt (g) | 19.92 ± 0.51 (11) | — | 14.90 ± 1.02 (4)* | — |
| Rep. Organ (g) | 0.48 ± 0.02 (11) | 2.42 | 0.27 ± 0.04 (4) | 1.78 |
| Brain (g) | 0.41 ± 0.01 (11) | 2.06 | 0.40 ± 0.01 (4) | 2.70 |
| Heart (g) | 0.12 ± 0.004 (11) | 0.61 | 0.12 ± 0.01 (4) | 0.81 |
| Liver (g) | 1.11 ± 0.04 (11) | 5.58 | 0.72 ± 0.06 (4)* | 4.85 |
| L. Kidney (g) | 0.14 ± 0.01 (11) | 0.68 | 0.10 ± 0.01 (4) | 0.65 |
| R. Kidney (g) | 0.13 ± 0.01 (10) | 0.67 | 0.10 ± 0.01 (4) | 0.65 |
| Spleen (g) | 0.11 ± 0.01 (11) | 0.53 | 0.11 ± 0.02 (4) | 0.72 |
| Thymus (g) | 0.08 ± 0.01 (11) | 0.42 | 0.085 ± 0.003 (4) | 0.57 |
| Gut (g) | 0.48 ± 0.03 (11) | 2.40 | 0.56 ± 0.07 (4) | 3.78 |
| Lung (g) | 0.19 ± 0.01 (11) | 0.97 | 0.16 ± 0.01 (4) | 1.06 |

| | RLX +/+ Female | % body wt | rlx −/− Female | % body wt |
|---|---|---|---|---|
| Body wt (g) | 16.68 ± 0.38 (11) | — | 13.15 ± 1.40 (5)* | — |
| Brain (g) | 0.41 ± 0.01 (11) | 2.48 | 0.40 ± 0.02 (5) | 3.07 |
| Heart (g) | 0.10 ± 0.003 (11) | 0.59 | 0.10 ± 0.003 (5) | 0.76 |
| Liver (g) | 0.90 ± 0.03 (11) | 5.39 | 0.57 ± 0.07 (5)* | 4.32 |
| L. Kidney (g) | 0.10 ± 0.004 (11) | 0.61 | 0.10 ± 0.003 (5) | 0.73 |
| R. Kidney (g) | 0.10 ± 0.003 (11) | 0.62 | 0.10 ± 0.01 (5) | 0.75 |
| Spleen (g) | 0.10 ± 0.01 (11) | 0.57 | 0.09 ± 0.01 (5) | 0.68 |
| Thymus (g) | 0.10 ± 0.010 (11) | 0.59 | 0.08 ± 0.003 (5) | 0.61 |
| Gut (g) | 0.50 ± 0.04 (11) | 2.97 | 0.51 ± 0.03 (5) | 3.86 |
| Lung (g) | 0.20 ± 0.01 (6) | 1.18 | 0.12 ± 0.01 (4) | 0.93 |

*=> $p < 0.05$

TABLE 8

Tissue Comparison of 3 month old mice (from RLX+/+ and RLX−/− parents, respectively), represented as Mean ± SE (n):

| | RLX +/+ Male | % body wt | rlx −/− Male | % body wt |
|---|---|---|---|---|
| Body wt (g) | 26.10 ± 0.51 (12) | — | 24.37 (1) | — |
| Rep. Organ (g) | 0.90 ± 0.03 (12) | 3.45 | 0.82 (1) | — |
| Brain (g) | 0.41 ± 0.01 (12) | 1.56 | 0.40 (1) | — |
| Heart (g) | 0.16 ± 0.003 (12) | 0.60 | 0.14 (1) | — |
| Liver (g) | 1.25 ± 0.04 (8) | 4.79 | 1.24 (1) | — |
| L. Kidney (g) | 0.20 ± 0.005 (12) | 0.75 | 0.17 (1) | — |
| R. Kidney (g) | 0.20 ± 0.004 (12) | 0.75 | 0.18 (1) | — |
| Spleen (g) | 0.085 ± 0.003 (12) | 0.33 | 0.08 (1) | — |
| Thymus (g) | 0.058 ± 0.004 (12) | 0.22 | 0.011 (1) | — |
| Gut (g) | 0.62 ± 0.05 (12) | 2.36 | 0.5 (1) | — |
| Lung (g) | 0.25 ± 0.02 (7) | 0.95 | 0.2 (1) | — |

| | RLX +/+ Female | % body wt | rlx −/− Female | % body wt |
|---|---|---|---|---|
| Body wt (g) | 22.30 ± 1.63 (12) | — | 23.73 ± 0.45 (5) | — |
| Brain (g) | 0.41 ± 0.01 (12) | 1.86 | 0.44 ± 0.01 (5) | 1.86 |
| Heart (g) | 0.13 ± 0.003 (12) | 0.59 | 0.14 ± 0.002 (5) | 0.61 |
| Liver (g) | 1.15 ± 0.05 (10) | 5.16 | 1.11 ± 0.003 (5) | 4.67 |
| L. Kidney (g) | 0.14 ± 0.004 (12) | 0.62 | 0.14 ± 0.003 (5) | 0.60 |
| R. Kidney (g) | 0.16 ± 0.005 (12) | 0.62 | 0.14 ± 0.01 (5) | 0.61 |
| Spleen (g) | 0.09 ± 0.004 (12) | 0.40 | 0.10 ± 0.01 (5) | 0.41 |
| Thymus (g) | 0.07 ± 0.003 (12) | 0.29 | 0.08 ± 0.010 (5) | 0.33 |
| Gut (g) | 0.55 ± 0.04 (12) | 2.45 | 0.68 ± 0.04 (5) | 2.86 |
| Lung (g) | 0.21 ± 0.01 (6) | 0.96 | 0.21 ± 0.005 (5) | 0.86 |

*=> $p < 0.05$

The Effects of Relaxin Gene Knockout on the Histology of Skin

The role of relaxin in the regulation of tissue remodeling was examined by studying the skin histology in rlx-null mice (rlx−/−). These mice were the progeny of rlx−/− male and female parents. Sequential skin samples from the ear and dorsum of the back of at least 5 male and 5 female mice were stained with H&E and Masson's trichrome stain and examined at each time point. Similar samples at the same time points were obtained from Rlx+/+ mice of the same strain. Upon histological examination of rlx-null mice, the dermis was found to have thickened progressively with time and had increased fibrosis throughout the dermis. Dermal samples of rlx-null mice were normal at one week of age; however, by one month early dermal fibrosis was evident. By 3 months of age there was a marked increase in dermal fibrosis that increased in density by 6 months of age. These dermal findings were similar in male and female rlx-null mice.

In these mice, the epidermis was normal, and hair was not altered, except for an initial lighter coat color in rlx-null mice that became indistinguishable from Rlx+/+ mice by one month of age. Examination of serum chemistries, hematological parameters and urine from the rlx-null mice were unremarkable.

These findings support previous observations that relaxin influences matrix turnover in vitro and in vivo by altering key matrix molecules, matrix-degrading enzymes and growth factors. Many stromal cells that produce interstitial collagens have relaxin receptors, whether derived from male or female sources. Antibody-based assays can detect relaxin in serum at the low picogram level in females during the luteal phase of the menstrual cycle, and these levels rise during pregnancy, a time when tissue remodeling is most evident. In contrast, serum relaxin is reported to be undetectable in males.

Rlx-null mice offer the first direct evidence that links relaxin to a generalized alteration of collagen turnover in normal skin. These results indicate that relaxin may be produced and circulate at biologically relevant concentrations below current levels of detection in males and females.

Relaxin participates in the ordered maintenance of matrix turnover in concert with other matrix-regulating molecules. Relaxin can influence tissue remodeling, promotion of blood vessel formation and stimulation of vasodilatation. These results also indicate that the relaxin synthetic pathway, and/or relaxin receptor, is associated with fibrotic conditions, such as scleroderma.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

The invention claimed is:

1. A method for stimulating maturation of an immature male reproductive tract tissue, comprising administering to a post-pubescent male subject having a low sperm count as compared with a normal sperm count an effective amount of a human relaxin agonist, wherein the human relaxin agonist is human relaxin H2 which is a heterodimeric polypeptide comprising a first polypeptide chain comprising:
   (i) amino acids 4 to 27 of SEQ ID NO:3;
   (ii) amino acids 4 to 28 of SEQ ID NO:3;
   (iii) amino acids 4 to 29 of SEQ ID NO:3;
   (iv) amino acids 4 to 30 of SEQ ID NO:3;
   (v) amino acids 4 to 31 of SEQ ID NO:3;
   (vi) amino acids 4 to 32 of SEQ ID NO:3;
   (vii) amino acids 4 to 33 of SEQ ID NO:3;
   (viii) amino acids 4 to 34 of SEQ ID NO:3;
   (ix) amino acids 4 to 35 of SEQ ID NO:3; or
   (x) amino acids 4 to 36 of SEQ ID NO:3 and
a second polypeptide chain comprising:
   (i) amino acids 4 to 27 of SEQ ID NO:4;
   (ii) amino acids 5 to 27 of SEQ ID NO:4; or
   (iii) amino acids 6 to 27 of SEQ ID NO:4 for a time period sufficient to stimulate tissue maturation, wherein said maturation is an increase in the number of viable sperm cells, as compared with tissue not contacted with the relaxin agonist.

2. The method of claim 1, wherein the tissue is testicular tissue.

3. The method of claim 1, wherein the human relaxin agonist is a recombinantly produced human relaxin H2 heterodimeric polypeptide comprising a first polypeptide chain comprising amino acids 4 to 36 of SEQ ID NO:3 and a second polypeptide chain comprising amino acids 4 to 27 of SEQ ID NO:4.

4. The method of claim 1, wherein the administering is by infusion, injection, oral delivery, nasal delivery, intrapulmonary delivery, rectal delivery, transdermal delivery, interstitial delivery or subcutaneous delivery.

5. The method of claim 4, wherein the administering is by delayed release delivery.

6. The method of claim 2, wherein the testicular tissue is epididymal tissue, seminiferous tissue, or sperm.

7. The method of claim 1, wherein the human relaxin agonist is a human H2 relaxin heterodimeric polypeptide with a truncated B chain (relaxin H2 (B29, A24); wherein the human H2 relaxin heterodimeric polypeptide comprises a first polypeptide chain comprising amino acids 4 to 32 of SEQ ID NO:3 and a second polypeptide chain comprising amino acids 4 to 27 of SEQ ID NO:4.

\* \* \* \* \*